(12) United States Patent
Ravichandran et al.

(10) Patent No.: US 7,173,128 B2
(45) Date of Patent: Feb. 6, 2007

(54) ULTRAVIOLET LIGHT ABSORBERS

(75) Inventors: Ramanathan Ravichandran, Suffern, NY (US); Stephen Daniel Pastor, Mayhill, NM (US); Deborah Judd, Poughkeepsie, NY (US); Joseph Edmund Babiarz, Amawalk, NY (US); Andrew Brian Naughton, Gipf-Oberfrick (CH); Mervin Gale Wood, Mobile, AL (US); Anthony David Debellis, Stony Point, NY (US); Rong Xiong, Dobbs Ferry, NY (US); Robert Edward Detlefsen, Putnam Valley, NY (US); Joseph Suhadolnik, Yorktown Heights, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 276 days.

(21) Appl. No.: 10/486,134

(22) PCT Filed: Aug. 5, 2002

(86) PCT No.: PCT/EP02/08709

§ 371 (c)(1),
(2), (4) Date: May 17, 2004

(87) PCT Pub. No.: WO03/016292

PCT Pub. Date: Feb. 27, 2003

(65) Prior Publication Data

US 2004/0192684 A1    Sep. 30, 2004

Related U.S. Application Data

(60) Provisional application No. 60/312,011, filed on Aug. 13, 2001.

(51) Int. Cl.
C07D 413/02 (2006.01)
C07D 265/22 (2006.01)
A61K 31/536 (2006.01)

(52) U.S. Cl. .................. 544/92; 544/73; 514/230.5
(58) Field of Classification Search .................. 544/92
See application file for complete search history.

(56) References Cited

U.S. PATENT DOCUMENTS

| | | | |
|---|---|---|---|
| 3,970,652 A | 7/1976 | Doyle, Jr. | 260/244 |
| 4,315,766 A | 2/1982 | Hamprecht et al. | 71/88 |
| 4,444,262 A | 4/1984 | Haskin et al. | 166/274 |
| 5,480,926 A | 1/1996 | Fagerburg et al. | 524/86 |
| 5,558,912 A | 9/1996 | Fagerburg et al. | 428/35.7 |
| 5,560,852 A | 10/1996 | Mura | 424/402 |
| 5,783,307 A | 7/1998 | Fagerburg et al. | 428/412 |

FOREIGN PATENT DOCUMENTS

| | | |
|---|---|---|
| DE | 2914915 | 10/1980 |
| EP | 0068327 | 1/1983 |
| EP | 0993965 | 4/2000 |
| WO | 99/48878 | 9/1999 |
| WO | WO 9948878 A1 * | 9/1999 |
| WO | 00/75139 | 12/2000 |

OTHER PUBLICATIONS

STN search printout for WO9948878A1 (Sep. 1999).*
Jakobsen et al. Bioorganic & Medicinal Chemistry 8 (2000) 2095-2103.*
P. Jakobsen et al., Bioorganic & Medicinal Chemistry, vol. 8, (2000), pp. 2095-2103.
G. Fenton et al., J. Med. Chem., vol. 32, (1989), pp. 265-272.
Chem. Abstr. 133:75546 for JP 00192394 (2000).
J. Gilmore et al., Bioorganic & Medicinal Chemistry Letters, vol. 6, No. 6. pp. 679-682 (1996).
Beilstein Registry No. 4573353 for F. Clemence et al., Heterocycl. Chem., vol. 21, (1984), pp. 1345-1353.
Beilstein Registry No. 1592485 for H. Crabtree et al, J. Chem. Soc. (1968), pp. 2730-2733.
Beilstein Registry No. 6874665 for E. Papadopoulos et al., Heterocycles, vol. 19, No. 6, (1982), pp. 1039-1042.

* cited by examiner

*Primary Examiner*—Kahsay Habte
(74) *Attorney, Agent, or Firm*—Tyler A. Stevenson

(57) ABSTRACT

The present invention relates to novel ultraviolet light absorbers of the benzoxazinone, oxanilide, benzylidene malonate, quinazoline and benzotriazole classes. The invention also relates to polymer and photographic compositions stabilized against the deleterious effects of light induced degradation which comprise the novel ultraviolet light absorbers.

3 Claims, No Drawings

ULTRAVIOLET LIGHT ABSORBERS

This is a 371 of PCT/EP02/08709, filed Aug. 5, 2002, which claims priority of U.S. provisional app. No. 60/312,011, filed Aug. 13, 2001.

The present invention relates to novel ultraviolet light absorbers of the benzoxazinone, oxanilide, benzylidene malonate, quinazoline and benzotriazole classes. The invention also relates to polymer and photographic compositions stabilized against the deleterious effects of light induced degradation, which comprise the novel ultraviolet light absorbers.

Benzoxazinones

U.S. Pat. Nos. 5,560,852, 5,783,307, 5,558,912, 5,480,926 and 4,444,262, EP 0 993 965 A2 and JP 00192394 disclose certain benzoxazinone ultraviolet light absorbers (UVA's). Examples of benzoxazinones for other uses can be found as in Fenton et al., J. Med. Chem. 1989, 32, 265–272 and WO 00/75139 A2. Most known benzoxazinone compounds are mono-substituted or symmetrically substituted.

The known mono-substituted or symmetrically substituted benzoxazinone UVA's are often associated with photopermanence, compatibility and/or volatility problems in polymeric substrates. It has been found that certain substituents such as alkyl, aralkyl, e.g. cumyl, and perfluoroalkyl provide these compounds with lower volatility and greater compatibility in a variety of polymeric systems. Other groups such as alkoxy and alkoxy carbonyl, among others, are also found to be useful. Further, it has been found that the permanence of benzoxazinone UV absorbers is enhanced or diminished depending on the electronic nature and substitution pattern of the substituents.

It has been found that for benzoxazinone compounds such as

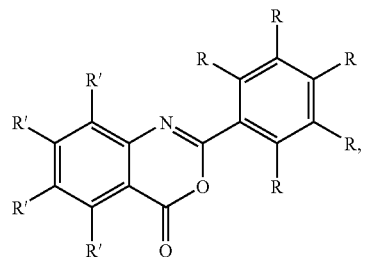

that electron withdrawing groups, such as —CF$_3$, cyano, carboxy ester, and the like, on the phenyl ring (R substituents) improve photostability, whereas electron rich substituents such as methoxy in these positions cause a decrease in photostability. This effect is particularly pronounced when certain other substituents are present on the benzo ring (R' groups), such as moderately electron donating groups. For example, it has been found that when at least one R' is a cumyl group (1,1-dimethylbenzyl), compatibility is improved while maintaining good photopermanence.

The benzoxazinone compounds of the present invention are of formula (Ia) or (Ib)

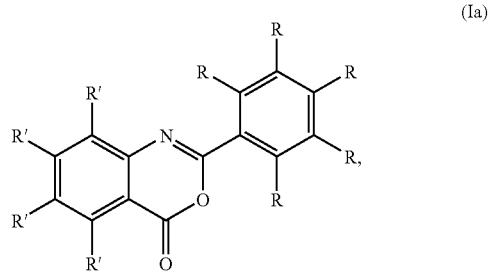

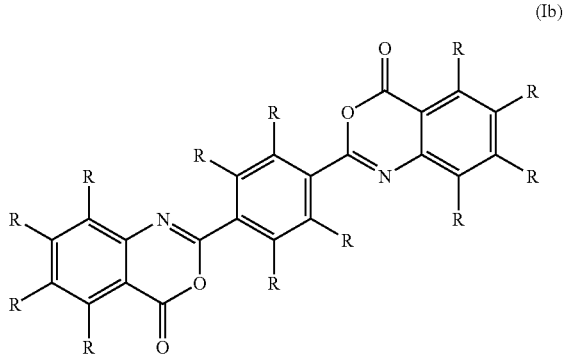

where in formula (Ia)

each R and R' is independently hydrogen, halogen, straight or branched chain alkoxy of 1 to 24 carbon atoms, cycloalkoxy of 5 to 12 carbon atoms, perfluoroalkoxy of 1 to 24 carbon atoms, cyano, perfluoroalkyl of 1 to 12 carbon atoms, —CO-G$_3$, —COOG$_3$, —CONHG$_3$, —CON(G$_3$)$_2$, E$_3$S—, E$_3$SO—, E$_3$SO$_2$—, nitro, —N(G$_3$)$_2$, G$_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, or each R and R' is independently hydroxy, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms;

or each R and R' is independently said alkyl of 1 to 24 carbon atoms or said alkoxy of 1 to 24 carbon atoms or said alkenyl of 2 to 18 carbon atoms substituted by one or more —OH, —COOG$_3$, —OCOG$_3$, —OE$_4$, —NCO, —NHCOG$_3$ or —NE$_7$E$_8$ groups or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, —NH$_2$ or —COOG$_3$ or mixtures thereof, or each R and R' is independently a group of formula

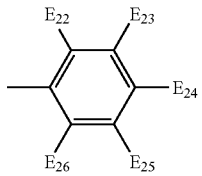

where
E$_{22}$, E$_{23}$, E$_{24}$, E$_{25}$ and E$_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOG$_3$, —OE$_4$, —NCO, —NHCOG$_3$ or —NE$_7$E$_8$, or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, or —NH$_2$, or mixtures thereof; or E$_{22}$, E$_{23}$, E$_{24}$, E$_{25}$ and E$_{26}$ are independently phenyl, phenylalkyl of 7 to 15 carbon atoms, —OH, —OCOG$_3$, —OE$_3$, —NCO, —NHCOG$_3$ or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —SO$_2$—X$_1$-E$_3$;

X$_1$ is —O—, —NH— or —NE$_4$-;

E$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, E$_7$ and E$_8$ are independently hydrogen, alkyl of 1 to 18 carbon atoms, C$_6$–C$_{14}$aryl, C$_7$–C$_{15}$aralkyl, straight or branched chain alkenyl of 2 to 18 carbon atoms, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring, or two adjacent R or R' groups together may form a 5 to 7 membered ring which may be interrupted by —O—, —NG$_3$- or —S—, which ring may be further substituted by straight or branched chain alkyl of 1–12 carbon atoms, aryl of 6 to 12 carbon atoms or phenylalkyl of 7 to 15 carbon atoms, where at least one R is halogen, cyano, perfluoroalkyl of 1 to 12 carbon atoms, —CO-G$_3$, —COOG$_3$, —CONHG$_3$, —CON(G$_3$)$_2$, E$_3$SO—, E$_3$SO$_2$—, nitro or a group

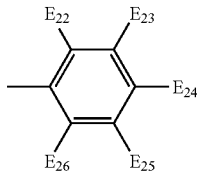

where at least one of E$_{22}$–E$_{26}$ is halogen, cyano, perfluoroalkyl of 1 to 12 carbon atoms, —CO-G$_3$, —COOG$_3$, —CONHG$_3$, —CON(G$_3$)$_2$, E$_3$SO—, E$_3$SO$_2$— or nitro; and where in formula (Ib)

at least one R is cyano or perfluoroalkyl of 1 to 12 carbon atoms and the remaining R groups are independently hydrogen, halogen, straight or branched chain alkoxy of 1 to 24 carbon atoms, cycloalkoxy of 5 to 12 carbon atoms, perfluoroalkoxy of 1 to 24 carbon atoms, cyano, perfluoroalkyl of 1 to 12 carbon atoms, —CO-G$_3$, —COOG$_3$, —CONHG$_3$, —CON(G$_3$)$_2$, E$_3$S—, E$_3$SO—, E$_3$SO$_2$—, nitro, —N(G$_3$)$_2$, G$_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, or each R is independently hydroxy, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms;

or each R is independently said alkyl of 1 to 24 carbon atoms or said alkoxy of 1 to 24 carbon atoms or said alkenyl of 2 to 18 carbon atoms substituted by one or more —OH, —COOG$_3$, —OCOG$_3$, —OE$_4$, —NCO, —NHCOG$_3$ or —NE$_7$E$_8$ groups or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, —NH$_2$ or —COOG$_3$ or mixtures thereof, or each R is Independently a group of formula

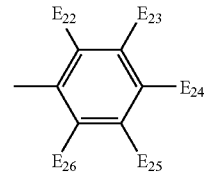

where
E$_{22}$, E$_{23}$, E$_{24}$, E$_{25}$ and E$_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOG$_3$, —OE$_4$, —NCO, —NHCOG$_3$ or —NE$_7$E$_8$, or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, or —NH$_2$, or mixtures thereof; or E$_{22}$, E$_{23}$, E$_{24}$, E$_{25}$ and E$_{26}$ are independently phenyl, phenylalkyl of 7 to 15 carbon atoms, —OH, —OCOG$_3$, —OE₃, —NCO, —NHCOG₃ or —NE₇E₈, cyano, nitro, perfluoroalkyl of 1 to 12 carbon atoms, —COG₃, —COOG₃, —CON(G₃)₂, —CONHG₃, E₃S—, E₃SO—, E₃SO₂—, —SO₂—X₁-E₃;

X₁ is —O—, —NH— or —NE₄-;

E₃ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, E₇ and E₈ are independently hydrogen, alkyl of 1 to 18 carbon atoms, C₆–C₁₄aryl, C₇–C₁₅aralkyl, straight or branched chain alkenyl of 2 to 18 carbon atoms, C₅–C₁₂cycloalkyl, C₆–C₁₄aryl or C₁–C₃hydroxylalkyl, or E₇ and E₈ together with the N atom are a pyrrolidine, piperidine, piperazine or morpholine ring, or two adjacent R groups together may form a 5 to 7 membered ring which may be interrupted by —O—, —NG₃- or —S—, which ring may be further substituted by straight or branched chain alkyl of 1–12 carbon atoms, aryl of 6 to 12 carbon atoms or phenylalkyl of 7 to 15 carbon atoms.

For instance, in the present benzoxazinone compounds of formula (Ia) above, when one of R is nitro, E₃SO₂—, —CO-G₃, —COOG₃, —CONHG₃, —CON(G₃)₂, at least one of R' is other than hydrogen. For example at least one of R' is cumyl.

For example, in the present benzoxazinone compounds of formula (Ia) above, at least one of R is cyano or perfluoroalkyl of 1 to 12 carbon atoms.

For example, at least one of R is —CF₃.

For example, at least one of R is cyano or perfluoroalkyl of 1 to 12 carbon atoms and at least one of R' is cumyl.

For example, more than one of R is halogen, for example 2, 3, 4 or 5 of R is halogen.

Present benzoxazinones are for example

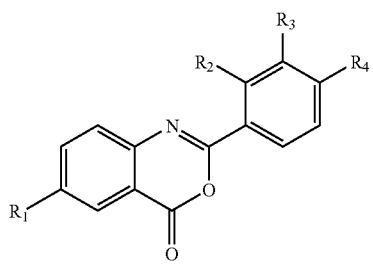

where

R₁, R₂, R₃ and R₄ are as defined above, in particular R₁ is cumyl or —OCH₃ and one of R₂, R₃ or R₄ is —CF₃ or —COOG₃, for example where:

| R₁ | R₂ | R₃ | R₄ | λmax |
|---|---|---|---|---|
| cumyl | H | H | COOCH₃ | 293 nm (ε 12500) |
| cumyl | H | H | CF₃ | 333 nm (ε 18750) |
| cumyl | H | COOCH₃ | H | 305 nm (ε 21200) |
| cumyl | H | CF₃ | H | 304 nm (ε 20500) |
| cumyl | CF₃ | H | H | 287 nm (ε 20200) |
| OCH₃ | H | CF₃ | H | 316 nm |
| OCH₃ | CF₃ | H | H | 291 nm |
| OCH₃ | H | H | CF₃ | 318 nm |

Further examples are compounds according to formula (Ib) which are for example of the formula

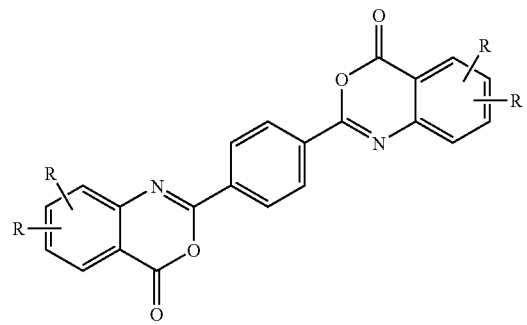

where

R is independently cyano, perfluoroalkyl of 1 to 12 carbon atoms, phenylalkyl of 7 to 15 carbon atoms, straight or branched chain alkyl of 1 to 24 carbon atoms or straight or branched chain alkoxy of 1 to 24 carbon atoms, The compound according to formula (Ib) may for example be of the formula

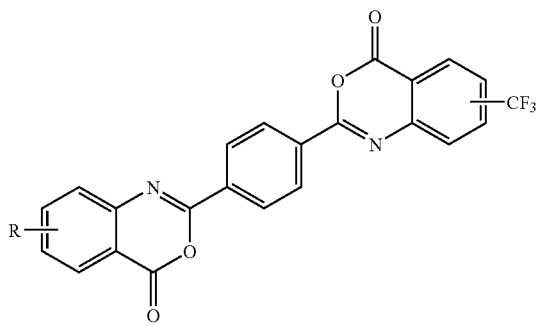

where

R is —CF₃ or cumyl.

The benzoxazinone compounds of formula (Ia) and (Ib) are useful UV-light stabilizers for organic materials. Consequently a further aspect of the invention is a composition comprising (a) an organic polymer or recording material subject to the adverse effects of ultraviolet light, and (b) at least one benzoxazinone compound of formula (Ia) or (Ib).

Oxanilides

The use and preparation of oxanilides as light stabilizers is well known and described for example in U.S. Pat. Nos. 3,906,041, 4,412,024, 5,045,083, 5,969,014 and 5,338,319. The use of oxanilides as ligands for transition metals are also known is disclosed in WO 98/40374. The use of certain unsymmetrical oxanilides (oxalamides) for improving solubility of the additive in polymer is taught in British Patent Application 1,234,128. The use of trifluoroalkyl substitutents, in particular trifluoromethyl, on symmetrical oxanilides for charge-control agents is described in JP 09179352. The use of trifluoroalkyl substituted symmetrical oxanilides for the stabilization of poly(vinyl chloride) is disclosed in Plast. Massy 1981 51–53 (in Russian) [Chem. Abstr. 1981 95 408186]. The preparation of oxanilides containing trifluoromethyl substituents is discribed in U.S.

Pat. No. 3,906,033, French 1 506 632, and French 1 516 276. The phytotoxicity of oxanilides containing trifluoromethyl substituents has been reported in Farmaco, Ed. Sci. 1967 22, 717 (in (Italian) [Chem. Abstr. 1968 68 77924]. The properties of the unsymmetrical oxanilides of the instant invention have not been previously anticipated, which includes 1) improved solubility, 2) improved compatibility and 3) in the case of the perfluoroalkyaryl compounds: improved molar absorptivity and spectral coverage. Additionally, a novel process for the preparation of the perfluoroalkyaryl compounds is described.

The present oxanilides are of formula (II)

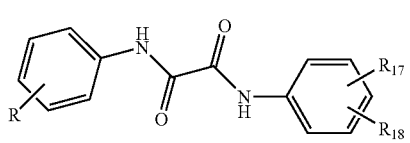
(II)

where R is straight or branched chain alkoxy of 12 to 24 carbon atoms and $R_{16}$ and $R_{17}$ are independently hydrogen, perfluoroalkyl of 1 to 12 carbon atoms, cyano, nitro, —CO-$G_3$, —COO$G_3$, —CONH$G_3$, —CON($G_3$)$_2$, $E_3$S—, $E_3$SO—, $E_3$SO$_2$—,

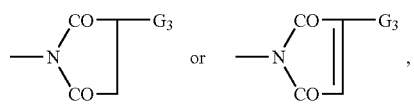

where both $R_{16}$ and $R_{17}$ are not hydrogen, $G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, and $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, or of the formula

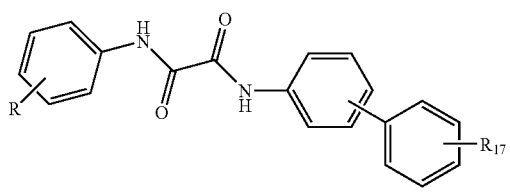

where R and $R_{17}$ are defined as above, where $R_{17}$ is not hydrogen.

The present oxanilides are for example unsymmetrical and are perflouroalkyl substituted.

The present oxanilides are for example

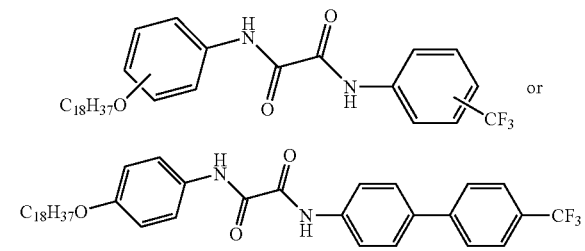
or

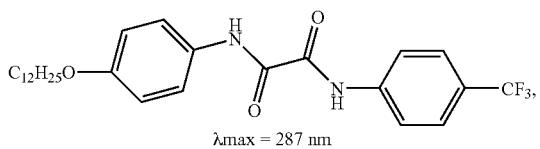

The present oxanilides are for example

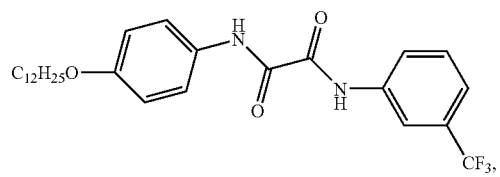

$\lambda max = 287$ nm

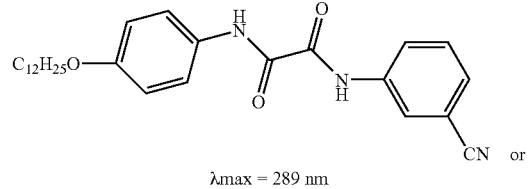

$\lambda max = 292$ nm

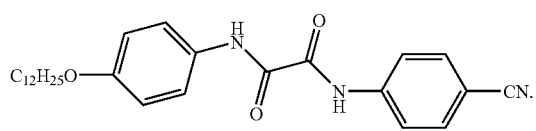
or $\lambda max = 289$ nm

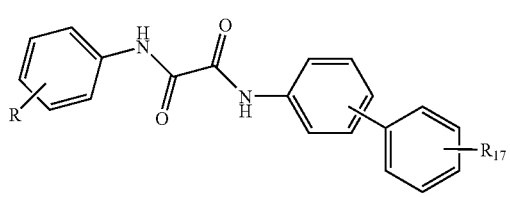

$\lambda max = 289$ nm

A further aspect of the invention is a composition comprising (a) an organic polymer or recording material subject to the adverse effects of ultraviolet light, and (b) at least one oxanilde compound of formula (II).

Yet another aspect of the invention is a process for the preparation of an aryl substituted oxanilide of the formula which process comprises adding together an arylboronic acid or ester of the formula

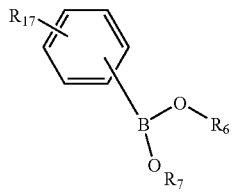

a halo- or tosyl-substituted oxalamide of the formula

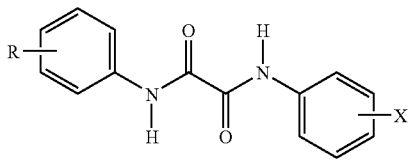

and a transition-metal-catalyst, and
reacting the mixture for an appropriate time at an appropriate temperature and pressure, where X is Cl, Br, I or tosyl, $R_6$ and $R_7$ are independently hydrogen, straight or branched chain alkyl of 1 to 12 carbon atoms, or together with the —OBO— group form a ring, R is straight or branched chain alkoxy of 12 to 24 carbon atoms, $R_{17}$ is perfluoroalkyl of 1 to 12 carbon atoms, cyano, nitro, —CO-$G_3$, —COO$G_3$, —CONH$G_3$,

—CON($G_3$)$_2$, $E_3$S—, $E_3$SO—, $E_3$SO$_2$—,

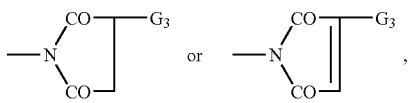

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, and $E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms.

For example $R_{17}$ is ortho, meta, or para substituted $C_1$-$C_{12}$ perfluoalkyl.

Definitions and preferences for the substituents have already been given and apply also for the process.

Preferably the catalyst is a palladium(II) catalyst and is present at a level from about 0.01 to to about 10 mole percent based on the arylboronic acid or ester compound.

For example the process comprises adding triphenylphosphine as a ligand.

In another embodiment the process comprises adding 1,1'-bis[2,4,8,10-tetrakis(1,1-dimethylethyl)-dibenzo[d,f][1,3,2]dioxa-phosphepin-6-yl]ferrocene as a ligand.

The present process may be anhydrous using dioxane as a solvent and potassium fluoride as a base.

The present process may use 1-propanol or 2-propanol as a solvent.

The present process is for example carried out between about 10 and about 100° C., for instance between about 50 and about 95° C., at atmospheric pressure.

Benzylidene Malonates

U.S. Pat. No. 3,706,701 specifies the use of methyl- and ethyl benzylidene malonates in which the substituent on the aromatic ring is a single methyl ether in the 4-position. Ether groups in the 4-position have advantages as they provide for a beneficial red-shift of the UV absorption and were shown to be more photochemically stable in cellulose acetate than where a methoxy group is present at the 2-position.

U.S. Pat. Nos. 4,260,732 and 4,404,257 also disclose benzylidene malonates.

U.S. Pat. Nos. 5,705,545 and 6,262,153 B1 disclose benzylidene malonates substituted with groups which contain hindered amine moieties.

U.S. Pat. No. 5,882,624 discloses a cosmetic/dermatological composition which includes a benzylidene malonate which can be substituted on the aryl ring by more than one alkoxy group. While generically the aryl can be substituted by up to three alkoxy groups in unspecified positions, the 3,4, and 5-positions are preferred and the 3,4-bis and 3-4-5-tris alkoxy derivatives are exemplified.

An advantage of providing a benzylidene malonate with more than one aryl substituent is that it allows one to shift the UV absorption spectra. It has been found that when more than one alkoxy group is present on the aryl ring, substitution at the 2-position is desirable for providing a maximum effect on UV absorption spectra. Furthermore, in contrast to the mono substituted derivatives described in U.S. Pat. No. 3,706,701, it has been found that in polyalkoxy derivatives substitution at the 2-position provides equal or better photostability than found in similar derivatives bearing a 3-alkoxy substituent.

U.S. Pat. No. 3,244,668 discloses substituted cinnamates and related compounds with a variety of substituents.

Accordingly, benzylidene malonates of this invention are of formula (III)

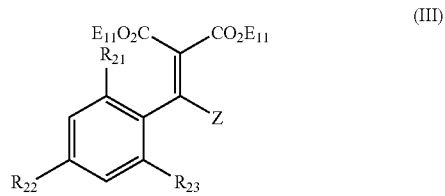

where $R_{21}$, $R_{22}$ and $R_{23}$ are independently hydrogen, straight or branched chain alkyl of 1 to 24 carbon atoms, straight or branched chain alkoxy 1 to 24 carbon atoms, or said alkyl or alkoxy substituted by one or more —OH, —COOE$_{11}$, —OCOE$_{11}$, —OE$_4$, —NHCOE$_{11}$ or —NE$_7$E$_8$ groups or mixtures thereof, where E$_4$ is straight or branched chain alkyl of 1 to 24 carbon atoms or straight or branched chain alkenyl of 2 to 18 carbon atoms;

where at least two of the $R_{21}$, $R_{22}$ and $R_{23}$ groups are alkoxy or substituted alkoxy;

$E_7$ and $E_8$ are independently hydrogen, alkyl of 1 to 18 carbon atoms, $C_6$–$C_{14}$aryl, $C_7$–$C_{15}$aralkyl, straight or branched chain alkenyl of 2 to 18 carbon atoms, $C_5$–$C_{12}$cycloalkyl, $C_6$–$C_{14}$aryl or $C_1$–$C_3$hydroxylalkyl, or $E_7$ and $E_8$ together with the N atom are a pyrrolidine, piperidine, piperazine or morpholine ring, $E_{11}$ is hydrogen, straight or branched chain $C_1$–$C_{24}$alkyl, said $C_1$–$C_{24}$alkyl substituted by 1 to 4 hydroxyl groups, $C_5$–$C_{12}$cycloalkyl or straight or branched chain $C_3$–$C_{18}$alkenyl;

or $E_{11}$ is a group

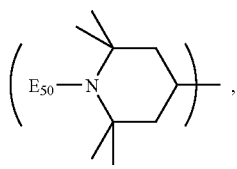

where $E_{50}$ is hydrogen, oxyl, straight or branched chain alkyl of 1 to 24 carbon atoms, straight or branched chain alkenyl of 3 to 24 carbon atoms, benzyl, acetyl, —$CH_2CH(OH)$-$E_{51}$, —$OE_{52}$, —$OE_{53}(OH)_b$, $E_{51}$ is hydrogen, methyl, ethyl or phenyl, $E_{52}$ is hydrogen, straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 12 carbon atoms or said aryl substituted by one to three alkyl of 1 to 4 carbon atoms;

$E_{53}$ is a straight or branched chain alkyl of 1 to 24 carbon atoms, cycloalkyl of 5 to 12 carbon atoms, cycloalkenyl of 5 to 12 carbon atoms, straight or branched chain alkenyl of 3 to 24 carbon atoms, phenylalkyl of 7 to 15 carbon atoms, aryl of 6 to 12 carbon atoms or said aryl substituted by one to three alkyl of 1 to 4 carbon atoms;

b is 1, 2 or 3 with the restriction that b cannot exceed the number of carbon atoms in $E_{53}$, and if b is 2 or 3, each hydroxyl group is attached to a different carbon atom of $E_{53}$; and z is hydrogen, straight or branched chain alkyl of 1 to 24 carbon atoms, phenyl or phenyl substituted by 1 to 4 straight or branched chain alkyl of 1 to 4 carbon atoms, straight or branched chain alkoxy of 1 to 12 carbon atoms, or said alkyl or alkoxy substituted by one or more —OH, —$COOE_{11}$, —$OCOE_{11}$, —$OE_4$, —NH-$COE_{11}$ or —$NE_7E_8$ groups or mixtures thereof, where $E_4$ is straight or branched chain alkyl of 1 to 24 carbon atoms or straight or branched chain alkenyl of 2 to 18 carbon atoms.

For example, at least two of $R_{21}$, $R_{22}$ and $R_{23}$ are alkoxy.

For example z is hydrogen.

For example $E_1$, is alkyl.

$R_{21}$, $R_{22}$ and $R_{23}$ are for example hydrogen, methoxy or methyl, for example where:

| $R_{21}$ | $R_{22}$ | $R_{23}$ |
|---|---|---|
| H | $OCH_3$ | $OCH_3$ |
| $OCH_3$ | H | $OCH_3$ |
| $OCH_3$ | $OCH_3$ | H |
| $OCH_3$ | $OCH_3$ | $OCH_3$ |
| $CH_3$ | $OCH_3$ | $OCH_3$ |
| $OCH_3$ | $CH_3$ | $OCH_3$ |
| $OCH_3$ | $OCH_3$ | $CH_3$ |

$R_{21}$, $R_{22}$ and $R_{23}$ are for example alkoxy alkoxy.

A further aspect of the invention is a composition comprising (a) an organic polymer or recording material subject to the adverse effects of ultraviolet light, and (b) at least one benzylidene malonate of formula (III).

Quinazolines

The novel quinazolines are of formula (IV)

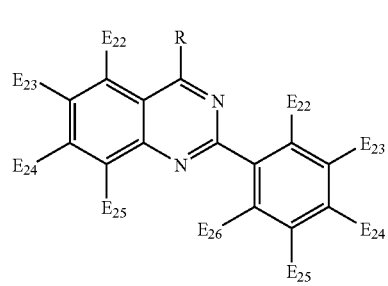

where

R is hydrogen, halogen, straight or branched chain thioether of 1 to 24 carbon atoms, straight or branched chain alkoxy of 1 to 24 carbon atoms, cycloalkoxy of 5 to 12 carbon atoms, phenoxy or phenoxy substituted by 1 to 4 alkyl of 1 to 4 carbon atoms, phenylalkoxy of 7 to 15 carbon atoms, perfluoroalkoxy of 1 to 24 carbon atoms, cyano, perfluoroalkyl of 1 to 12 carbon atoms, —CO-$G_3$, —$COOG_3$, —$CONHG_3$, —$CON(G_3)_2$, $E_3S$—, $E_3SO$—, $E_3SO_2$—, nitro, —$P(O)(C_6H_5)_2$, —$P(O)(OG_3)_2$,

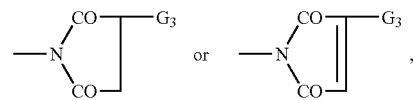

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, or R is hydroxy, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms;

or R is said alkyl of 1 to 24 carbon atoms or or said alkoxy of 1 to 24 carbon atoms or said alkenyl of 2 to 18 carbon atoms substituted by one or more —OH, —COOE$_{11}$, —OCOE$_{11}$, —OE$_4$, —NCO, —NHCOE$_{11}$, —NE$_7$E$_8$ or

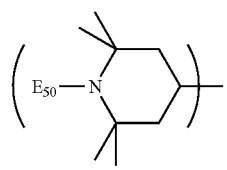

groups or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, —OE$_4$, —NH$_2$ or —COOE$_{11}$, or

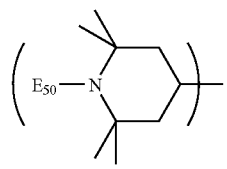

groups or mixtures thereof, or R is a group of formula

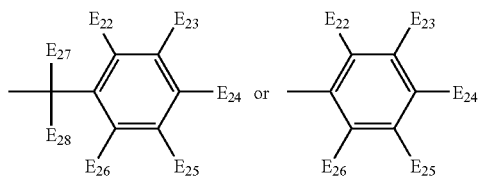

where

E$_{27}$ and E$_{28}$ are independently alkyl of 1 to 18 carbon atoms, or cycloalkyl of 5 to 12 carbon atoms;

E$_{22}$, E$_{23}$, E$_{24}$, E$_{25}$ and E$_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOE$_{11}$, —OE$_4$, —NCO, —NHCOE$_{11}$ or —NE$_7$E$_8$, or mixtures thereof, where E$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, or —NH$_2$, or mixtures thereof; or E$_{22}$, E$_{23}$, E$_{24}$, E$_{25}$ and E$_{26}$ are independently phenyl, phenylalkyl of 7 to 15 carbon atoms, —OH, —OCOE$_{11}$, —OE$_{29}$, —NCO, —NHCOE$_{11}$ or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —P(O)(C$_6$H$_5$)$_2$,

—P(O))OG$_3$)$_2$, —SO$_2$—X$_1$-E$_{29}$;

X$_1$ is —O—, —NH— or —NE$_4$-;

E$_{29}$ is straight or branched chain alkyl of 1 to 24 carbon atoms, straight or branched chain alkenyl of 2 to 18 carbon atoms, said alkyl or said alkenyl substituted by one or more —OH, —OCOE$_{11}$, —OE$_4$, —NCO, —NHCOE$_{11}$, —NE$_7$E$_8$, phthalimido,

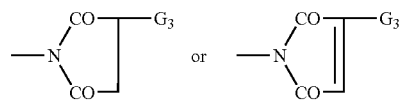

mixtures thereof, where E$_4$ is straight or branched chain alkyl of 1 to 24 carbon atoms or alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, or —NH$_2$, or mixtures thereof; or E$_{29}$ is aryl of 6 to 12 carbon atoms or phenylalkyl of 7 to 15 carbon atoms, or said aryl or said phenylalkyl substituted by one to three alkyl groups of 1 to 4 carbon atoms;

E$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, E$_7$ and E$_8$ are independently hydrogen, alkyl of 1 to 18 carbon atoms, straight or branched chain C$_3$–C$_{18}$alkyl which is interrupted by —O—, —S— or —NE$_{11}$, straight or branched chain alkenyl of 2 to 18 carbon atoms, C$_5$–C$_{12}$cycloalkyl, C$_6$–C$_{14}$aryl or C$_1$–C$_3$hydroxylalkyl, or E$_7$ and E$_8$ together with the N atom are a pyrrolidine, piperidine, piperazine or morpholine ring, or E$_{11}$ is hydrogen, straight or branched chain C$_1$–C$_{24}$alkyl, C$_5$–C$_{12}$cycloalkyl, straight or branched chain C$_3$–C$_{18}$alkenyl, C$_6$–C$_{14}$aryl or C$_7$–C$_{15}$aralkyl; or said alkyl substituted by one or more

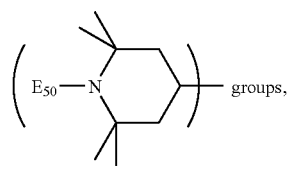

groups,

E$_{50}$ is hydrogen, oxyl, straight or branched chain alkyl of 1 to 24 carbon atoms, straight or branched chain alkenyl of 3 to 24 carbon atoms, benzyl, acetyl, —CH$_2$CH(OH)-E$_{51}$, —OE$_{52}$, —OE$_{53}$(OH)$_b$, E$_{51}$ is hydrogen, methyl, ethyl or phenyl, E$_{52}$ is hydrogen, straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 12 carbon atoms or said aryl substituted by one to three alkyl of 1 to 4 carbon atoms; or a group of formula

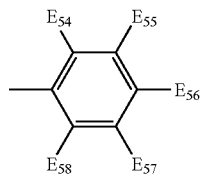

$E_{53}$ is a straight or branched chain alkyl of 1 to 24 carbon atoms, cycloalkyl of 5 to 12 carbon atoms, cycloalkenyl of 5 to 12 carbon atoms, straight or branched chain alkenyl of 3 to 24 carbon atoms, phenylalkyl of 7 to 15 carbon atoms, aryl of 6 to 12 carbon atoms or said aryl substituted by one to three alkyl of 1 to 4 carbon atoms;

b is 1, 2 or 3 with the restriction that b cannot exceed the number of carbon atoms in $E_{53}$, and if b is 2 or 3, each hydroxyl group is attached to a different carbon atom of $E_{53}$; and $E_{54}$ to $E_{58}$ are independently hydrogen, halogen, nitro, cyano, alkyl of 1 to 18 carbon atoms, phenylalkyl of 7 to 15 carbon atoms, aryl of 6 to 12 carbon atoms, hydroxyl, carboxyl, alkylthio of 1 to 18 carbon atoms, straight or branched chain alkoxy of 1 to 18 carbon atoms, cycloalkoxy of 5 to 12 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring.

Quinazolines of the present invention are for example

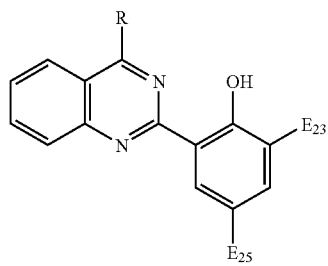

where $E_{23}$ is phenylalkyl of 7 to 15 carbon atoms and $E_{25}$ is straight or branched chain alkyl of 1 to 18 carbon atoms.

For example, the present quinazolines are of the formula

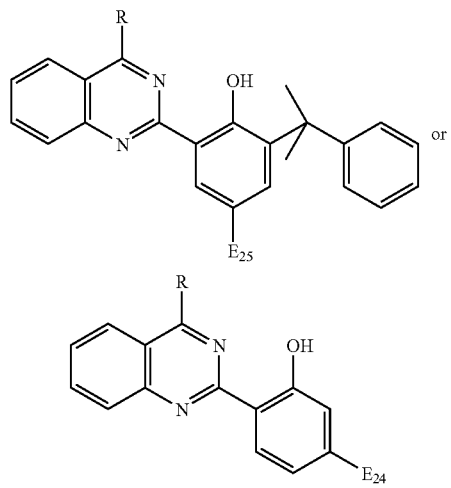

where $E_{25}$ is straight or branched chain alkyl of 1 to 18 carbon atoms and $E_{24}$ is straight or branched chain alkoxy of 1 to 24 carbon atoms.

For example of the formula

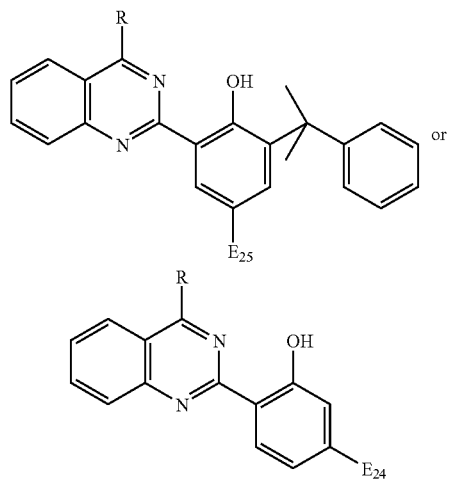

where $E_{25}$ is straight or branched chain alkyl of 1 to 18 carbon atoms, $E_{24}$ is straight or branched chain alkoxy of 1 to 24 carbon atoms and R is hydrogen, straight or branched chain alkyl of 1 to 24 carbon atoms, aryl of 6 to 12 carbon atoms or aryl substituted by 1 to 4 alkyl of 1 to 4 carbon atoms, straight or branched chain alkoxy of 1 to 24 carbon atoms, halogen, cyano, perfluoroalkyl of 1 to 12 carbon atoms, $E_3S—$, $E_3SO—$, $E_3SO_2—$ or biphenyl.

For example, the present quinazolines are

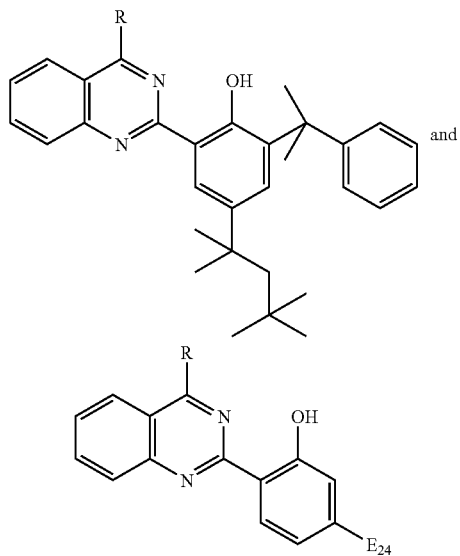

where $E_{24}$ is straight or branched chain alkoxy of 1 to 24 carbon atoms and

R is hydrogen, $CH_3$, phenyl, —$OCH_3$, Cl, —CN, —$CF_3$, —SPh, —$SO_2$Ph or biphenyl.

Also an aspect of the invetion is a composition comprising (a) an organic polymer or recording material subject to the adverse effects of ultraviolet light, and (b) at least one quinazoline compound of formula (IV).

Benzotriazoles

Phenolic benzotriazole, that is ortho-hydroxyphenyl-2H-benzotriazole, ultraviolet light absorbers have long been known and have achieved commercial success as stabilizers for polymer substrates, for example in thermoplastic articles and coating compositions.

Non-phenolic benzotriazole ultraviolet light absorbers (UVA's) are unknown. Non-phenolic benzotriazole additives may provide certain advantages or properties not achievable with phenolic UVA's. It has been discovered that certain non-phenolic compounds of the benzotriazole classe are suitable as ultraviolet light absorbers.

The novel benzotriazoles of the present invention are represented by formula (V)

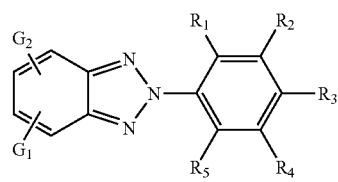

(V)

in which $G_1$ and $G_2$ are independently hydrogen, halogen, straight or branched chain thioether of 1 to 24 carbon atoms, straight or branched chain alkoxy of 1 to 24 carbon atoms, cycloalkoxy of 5 to 12 carbon atoms, phenoxy or phenoxy substituted by 1 to 4 alkyl of 1 to 4 carbon atoms, phenylalkoxy of 7 to 15 carbon atoms, perfluoroalkoxy of 1 to 24 carbon atoms, cyano, perfluoroalkyl of 1 to 12 carbon atoms, —CO-$G_3$, —COO$G_3$, —CONH$G_3$, —CON($G_3$)$_2$, $E_3$S—, $E_3$SO—, $E_3$SO$_2$—, nitro, —P(O)($C_6H_5$)$_2$, —P(O)(O$G_3$)$_2$,

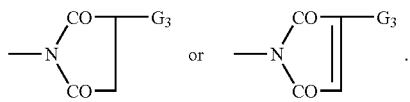

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, $R_2$, $R_3$ and $R_4$ are independently hydrogen, hydroxy, straight or branched chain alkyl of 1 to 24 carbon atoms, straight or branched chain alkoxy of 1 to 24 carbon atoms, cycloalkoxy of 5 to 12 carbon atoms, phenoxy or phenoxy substituted by 1 to 4 alkyl of 1 to 4 carbon atoms, phenylalkoxy of 7 to 15 carbon atoms, straight or branched chain alkenyl of 2 to 24 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms;

or $R_2$, $R_3$ and $R_4$ are independently said alkyl of 1 to 24 carbon atoms or said alkenyl of 2 to 18 carbon atoms substituted by one or more —OH, —COO$E_{11}$, —OCO$E_{11}$, —O$E_4$, —NCO, —NHCO$E_{11}$, —N$E_7E_8$ or

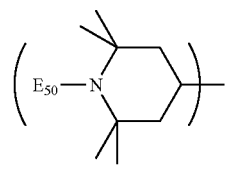

groups or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —N$E_4$- groups or mixtures thereof and which can be unsubstituted or substituted by one or more —OH, —NH$_2$ or —COO$E_{11}$ or

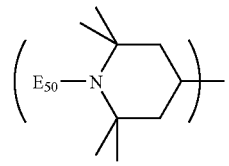

groups or mixtures thereof, or $R_1$, $R_2$ and $R_4$ are independently a group of formula

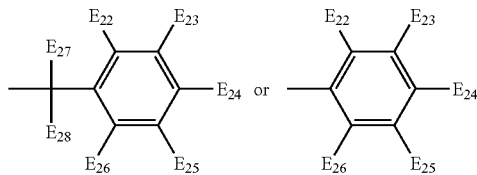

where $E_{27}$ and $E_{28}$ are independently alkyl of 1 to 18 carbon atoms, or cycloalkyl of 5 to 12 carbon atoms;

$E_{22}$, $E_{23}$, $E_{24}$, $E_{25}$ and $E_{26}$ are independently hydrogen, halogen, straight or branched alkyl of 1 to 18 carbon atoms, alkenyl of 2 to 18 carbon atoms, said alkyl or said alkenyl substituted by one or more halogen, —$OCOE_{11}$, —$OE_4$, —NCO, —$NHCOE_{11}$, or —$NE_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —$NE_4$- groups or mixtures thereof and which can be unsubstituted or substituted by one or more —OH, or —$NH_2$, or mixtures thereof; or $E_{22}$, $E_{23}$, $E_{24}$, $E_{25}$ and $E_{26}$ are independently phenyl, phenylalkyl of 7 to 15 carbon atoms, —OH, —$OCOE_{11}$, —$OE_{29}$, —NCO, —$NHCOE_{11}$ or —$NE_7E_8$, cyano, nitro, perfluoroalkyl of 1 to 12 carbon atoms, —$COG_3$, —$COOG_3$, —$CON(G_3)_2$, —$CONHG_3$, $E_3S$—, $E_3SO$—, $E_3SO_2$—, —$P(O)(C_6H_5)_2$,

—$P(O))OG_3)_2$, —$SO_2$—$X_1$-$E_{29}$;

$X_1$ is —O—, —NH— or —$NE_4$-;

$E_{29}$ is straight or branched chain alkyl of 1 to 24 carbon atoms, straight or branched chain alkenyl of 2 to 18 carbon atoms, said alkyl or said alkenyl substituted by one or more —OH, —$OCOE_{11}$, —$OE_4$, —NCO, —$NHCOE_{11}$, —$NE_7E_8$, phthalimido,

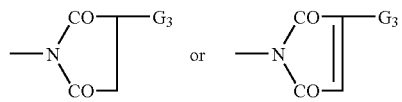

or mixtures thereof, where $E_4$ is straight or branched chain alkyl of 1 to 24 carbon atoms or alkenyl of 2 to 18 carbon atoms; or said alkyl or said alkenyl interrupted by one or more —O—, —NH— or —$NE_4$- groups or mixtures thereof and which can be unsubstituted or substituted by one or more —OH, or —$NH_2$, or mixtures thereof; or $E_{29}$ is aryl of 6 to 12 carbon atoms or phenylalkyl of 7 to 15 carbon atoms, or said aryl or said phenylalkyl substituted by one to three alkyl groups of 1 to 4 carbon atoms;

$E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, $E_7$ and $E_8$ are independently hydrogen, alkyl of 1 to 18 carbon atoms, straight or branched chain $C_3$–$C_{18}$alkyl which is interrupted by —O—, —S— or —$NE_{11}$-, straight or branched chain alkenyl of 2 to 18 carbon atoms, $C_5$–$C_{12}$cycloalkyl, $C_5$–$C_{14}$aryl or $C_1$–$C_3$hydroxylalkyl, or $E_7$ and $E_8$ together with the N atom are a pyrrolidine, piperidine, piperazine or morpholine ring, or $E_{11}$ is hydrogen, straight or branched chain $C_1$–$C_{24}$alkyl, $C_5$–$C_{12}$cycloalkyl, straight or branched chain $C_2$–$C_{18}$alkenyl, $C_5$–$C_{14}$aryl or $C_7$–$C_{15}$aralkyl; or said alkyl substituted by one or more

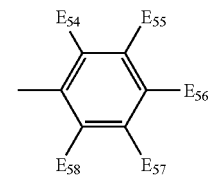

groups, $E_{50}$ is hydrogen, oxyl, straight or branched chain alkyl of 1 to 24 carbon atoms, straight or branched chain alkenyl of 3 to 24 carbon atoms, benzyl, acetyl, —$CH_2CH(OH)$-$E_{51}$, —$OE_{52}$, —$OE_{53}(OH)_b$, $E_{51}$ is hydrogen, methyl, ethyl or phenyl, $E_{52}$ is hydrogen, straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 12 carbon atoms or said aryl substituted by one to three alkyl of 1 to 4 carbon atoms; or a group of formula $E_{53}$ is a straight or branched chain alkyl of 1 to 24 carbon atoms, cycloalkyl of 5 to 12 carbon atoms, cycloalkenyl of 5 to 12 carbon atoms, straight or branched chain alkenyl of 3 to 24 carbon atoms, phenylalkyl of 7 to 15 carbon atoms, aryl of 6 to 12 carbon atoms or said aryl substituted by one to three alkyl of 1 to 4 carbon atoms;

b is 1, 2 or 3 with the restriction that b cannot exceed the number of carbon atoms in $E_{53}$, and if b is 2 or 3, each hydroxyl group is attached to a different carbon atom of $E_{53}$;

$E_{54}$ to $E_{58}$ are independently hydrogen, halogen, nitro, cyano, alkyl of 1 to 18 carbon atoms, phenylalkyl of 7 to 15 carbon atoms, aryl of 6 to 12 carbon atoms, hydroxyl, carboxyl, alkylthio of 1 to 18 carbon atoms, straight or branched chain alkoxy of 1 to 18 carbon atoms, cycloalkoxy of 5 to 12 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring;

R₁ and R₅ are independently as defined for R₂, R₃ and R₄, with the proviso that neither may be hydroxy;

or R₁ and R₂ together may form a 5 to 7 membered ring which may be interrupted by —O—, —NG₃- or —S—, which ring may be further substituted by straight or branched chain alkyl of 1–12 carbon atoms, aryl of 6 to 12 carbon atoms or phenylalkyl of 7 to 15 carbon atoms.

For example, the present benzotriazoles are of the formula

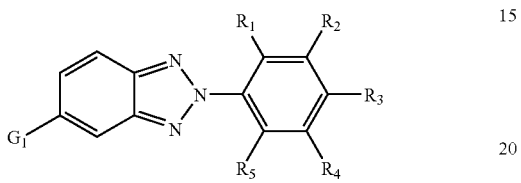

where
G₁ is hydrogen or perfluoroalkyl of 1 to 12 carbon atoms,
R₂ is hydrogen or straight or branched chain alkyl of 1 to 24 carbon atoms,
R₃ is hydrogen, hydroxy or straight or branched chain alkoxy of 1 to 24 carbon atoms,
R₄ is hydrogen or straight or branched chain alkyl of 1 to 24 carbon atoms,
R₅ is hydrogen or straight or branched chain alkyl of 1 to 24 carbon atoms and
R₁ is straight or branched chain alkyl of 1 to 24 carbon atoms or straight or branched chain alkoxy of 1 to 24 carbon atoms.

For example, the present benzotriazole compounds are of the formula

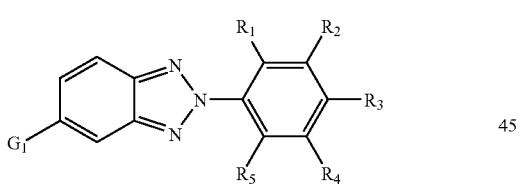

where
G₁ is hydrogen or —CF₃,
R₂ is hydrogen or —CH₃,
R₃ is hydrogen, hydroxy or —OCH₃,
R₄ is hydrogen, tert-butyl or —CH₃,
R₅ is hydrogen or —CH₃ and
R₁ is —CH₃ or —OCH₃.

Specific examples of benzotriazoles of the present invention are

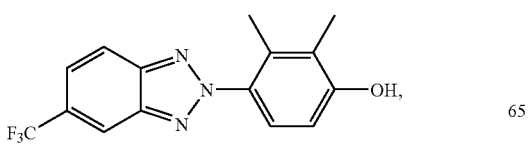

-continued

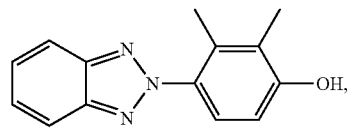

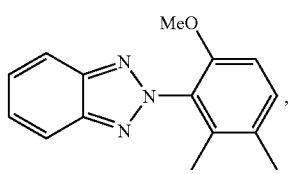

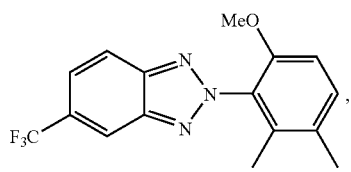

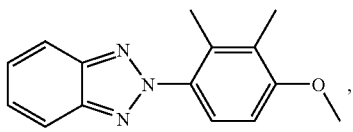

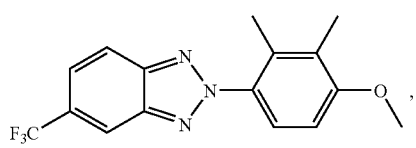

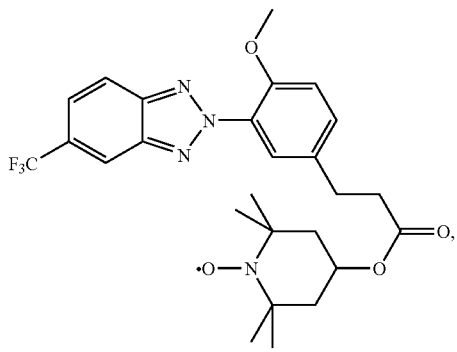

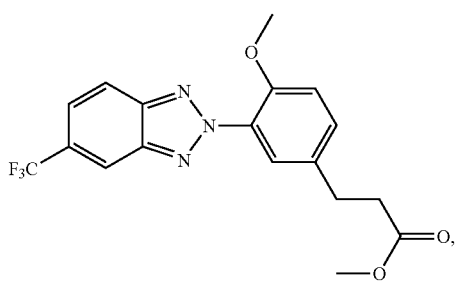

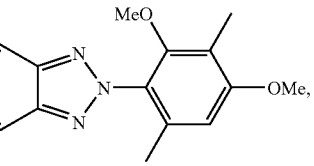

-continued

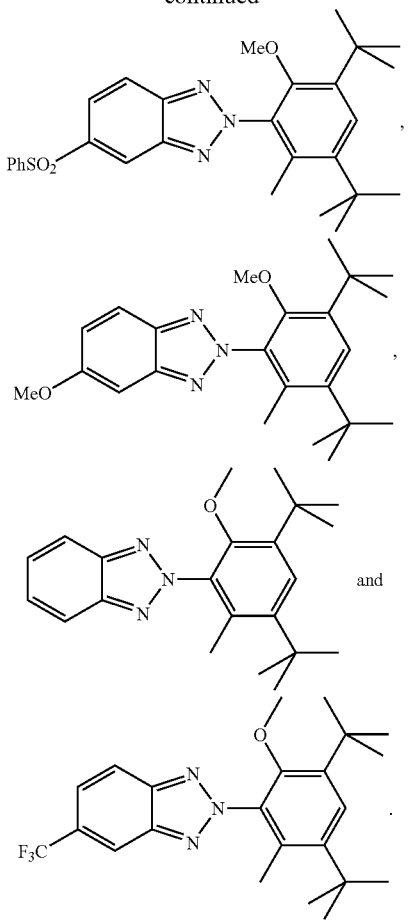

Present benzotriazoles are for example

| $G_1$ | $R_2$ | $R_3$ | $R_4$ | $R_5$ | $R_1$ |
|---|---|---|---|---|---|
| H | H | OH | t-butyl | H | $CH_3$ |
| H | H | $OCH_3$ | t-butyl | H | $CH_3$ |
| $CF_3$ | $CH_3$ | OH | H | H | $CH_3$ |
| $CF_3$ | $CH_3$ | $OCH_3$ | H | H | $CH_3$ |
| H | $CH_3$ | OH | H | H | $CH_3$ |
| H | $CH_3$ | $OCH_3$ | H | H | $CH_3$ |
| H | H | H | $CH_3$ | $CH_3$ | $OCH_3$ |
| $CF_3$ | H | H | $CH_3$ | $CH_3$ | $OCH_3$ |

For example, present benzotriazoles have substituents (groups other than hydrogen) in both the $R_1$ and $R_5$ positions of the phenyl ring, the ortho, ortho positions.

Yet another aspect of the invention is a composition comprising
(a) an organic polymer or recording material subject to the adverse effects of ultraviolet light, and
(b) at least one benzotriazole compound of formula (M).

In the present compounds:

Straight or branched chain alkyl is for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

Cycloalkyl or susbstituted cycloalkyl is for example cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl.

Aryl is for example phenyl, biphenyl and napthyl.

Aryl substituted by alkyl is for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Phenylalkyl is for example, benzyl, α-methylbenzyl, α,α-dimethylbenzyl or 2-phenyl-ethyl. Cumyl is α,α-dimethylbenzyl or α-cumyl.

Phenylalkyl or substituted phenylalkyl is for example 2-methylbenzyl, 3-methylbenzyl, 4-methylbenzyl, 2,4-dimethylbenzyl, 2,6-dimethylbenzyl or 4-tert-butylbenzyl.

Straight or branched chain alkoxy is for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy.

Cycloalkoxy is for example, cyclopentyloxy, methylcyclopentyloxy, dimethylcyclopentyloxy, cyclohexyloxy, methylcyclohexyloxy, dimethylcyclohexyloxy, trimethylcyclohexyloxy, tert-butylcyclohexyloxy, cycloheptyloxy or cyclooctyloxy.

Phenoxy substituted by one to three alkyl is for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Phenylalkoxy of 7 to 15 carbon atoms is for example, benzyloxy, α-methylbenzyloxy, α,α-dimethylbenzyloxy or 2-phenylethoxy.

Straight or branched chain alkylthio (thioether) is for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

The present invention also relates to compositions stabilized against the deleterious effects of ultraviolet radiation which comprise the present novel ultraviolet light absorbers.

Accordingly, the present invention is also directed to a composition comprising
(a) an organic polymer or recording material subject to the adverse effects of ultraviolet light, and
(b) at least one compound selected from the present benzoxazinone, oxanilide, benzylidene malonate, quinazoline and benzotriazole compounds.

The polymer substrates of component (a) are natural or synthetic polymers or copolymers. The substrates of component (a) are for example synthetic polymers, in particular thermoplastic polymers such as polyamides and polyolefins. Polyolefins are for instance polypropylene or polyethylene.

Suitable polymer substrates of component (a) are for example:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
   a) radical polymerization (normally under high pressure and at elevated temperature).
   b) catalytic polymerization using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EM and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, SAN, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 619, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS. Polyesters and polyester copolymers as defined in U.S. Pat. No. 5,807,932 (column 2, line 53), incorporated herein by reference.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastc PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.
32. Polysiloxanes such as the soft, hydrophilic polysiloxanes described, for example, in U.S. Pat. No. 4,259,467; and the hard polyorganosiloxanes described, for example, in U.S. Pat. No. 4,355,147.
33. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

34. Radiation curable compositions containing ethylenically unsaturated monomers or oligomers and a polyunsaturated aliphatic oligomer.

35. Epoxymelamine resins such as light-stable epoxy resins crosslinked by an epoxy functional coetherified high solids melamine resin such as LSE-4103 (Monsanto).

Materials that are stabilized according to the instant invention include recording materials such as photographic reproductions or reprographic materials. The novel recording materials also include, for example, pressure-sensitive copying systems, microcapsule photocopier systems, heat-sensitive copier systems, photographic material and ink-jet printing.

Materials stabilized according to the present invention include thermoplastic molded articles, fibers and films.

Materials stabilized according to the present invention include automotive coatings.

Compositions stabilized according to the present invention also include photographic materials, polyolefin articles exposed to chlorine, gamma-irradiated polyolefins, woven or nonwoven polyolefin fibers or fabrics, polyolefin hollow article prepared by the rotomolding process, recycled plastics, coextruded films over PVC, PC or ABS, multilayer polymer structures, and radiation-cured inks or coatings.

Further in addition to component (b), the present stabilized compositions may comprise other traditional additives selected from, for example, other antioxidants, other UV absorbers, other hindered amines, other phosphites or phosphonites, benzofuran-2-ones, thiosynergists, polyamide stabilizers, metal stearates, nucleating agents, fillers, reinforcing agents, lubricants, emulsifiers, dyes, pigments, optical brighteners, flame retardants, antistatic agents, blowing agents and the like, such as the materials listed below, or mixtures thereof. These optional further additives are present from about 0.01 to about 10% by weight; for example from about 0.025 to about 5% by weight, for instance from about 0.1 to about 3% by weight, based on the total weight of the composition.

These other traditional additives are selected from, for example:

1. Antioxidants
  1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-di-methyl-6-(1-methylheptadec-1-yl)phenol, 2,4-dimethyl-6-(1-methyltridec-1-yl)phenol and mixtures thereof.
  1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol;
  1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.
  1.4. Tocopherols, for example $\alpha$-tocopherol, $\beta$-tocopherol, $\gamma$-tocopherol, $\delta$-tocopherol and mixtures thereof (Vitamin E).
  1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.
  1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methylphenyl)dicyclopentadiene, bis[2-(3'-tert-butyl-2-hydroxy-5-methylbenzyl)-6-tert-butyl-4-methylphenyl] terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methylphenyl)pentane.
  1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl)sulfide, 3,5-di-tert-butyl-4-hydroxybenzyl-mercapto-acetic acid isooctyl ester, bis-(4tert-butyl-3-hydroxy-2,6-dimethylbenzyl)dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.
  1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)malonate, di-dodecylmercaptoethyl-2,2-bis-(3,5-di-tert-butyl-4-hydroxybenzyl)malonate, bis-[4-(1, 1,3,3-tetramethylbutyl)phenyl]-2,2-bis(3,5-di-tert-butyl-4-hydroxybenzyl)malonate.
  1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
  1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis (3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N',N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987, 5,977,219 and 6,166,218 such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy) carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotdazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzorhenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS# 7443-25-6), and Sanduvor® PR31, di-(1,2,2,6,6-pentamethylpiperidin-4-yl)p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethyl-piperidyl)succinate, linear or cyclic condensates of N,N'-bis-(2,2,6,6-tetramethyl-4-piperidyl)-hexamethylenediamine and 4-morpholino-2,6dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2, 6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described U.S. Pat. No. 5,980,783, the relevant parts of which are hereby incorporated by reference, that is compounds of component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-1, 1g-2 or 1-k-1 listed on columns 64–72 of said U.S. Pat. No. 5,980,783.

The sterically hindered amine may also be one of the compounds described in EP 782994, for example compounds as described in claims 10 or 38 or in Examples 1–12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethyl-piperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperdin-4-yl]-N-butylamino}-6-(2-hydroxyethylamino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, and U.S. application Ser. No. 09/383,163, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxy-ethoxy)phenyl]-6-(2,4-dimethylphenyl)-s-triazine, 2,4-bis[2-hydroxy-4-(2-hydroxyethoxy)-phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine, 2,4-bis(2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)-phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2] dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl)phosphite (Irgafos®168, Ciba Specialty Chemicals Corp.), tris(nonylphenyl)phosphite, 7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

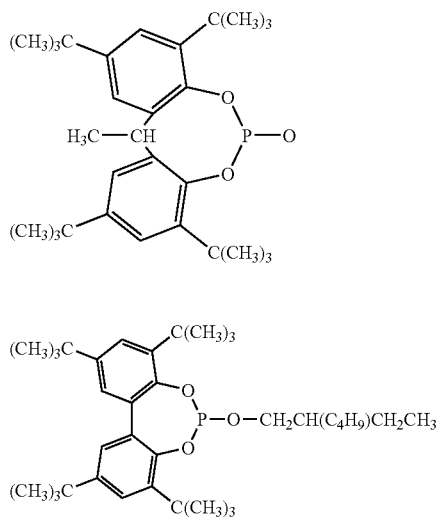
(A)

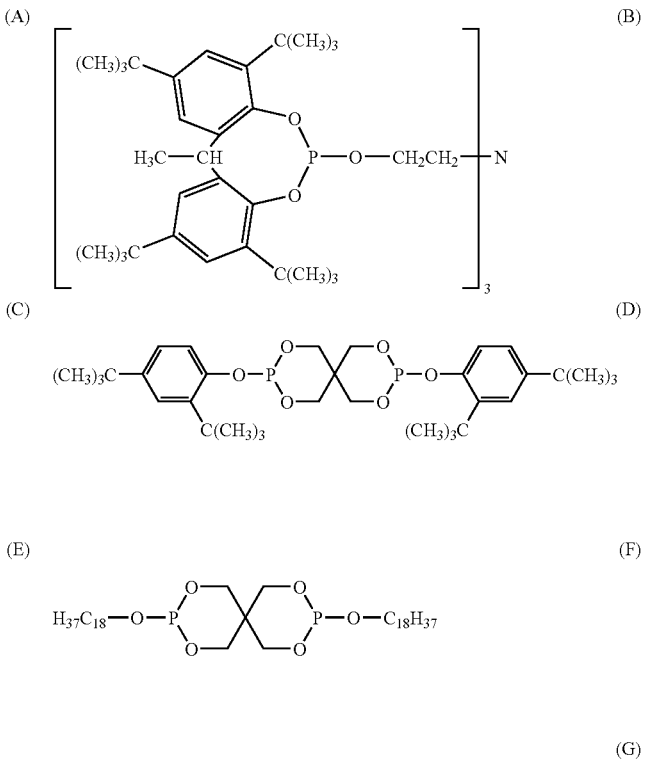
(B)

(C)

(D)

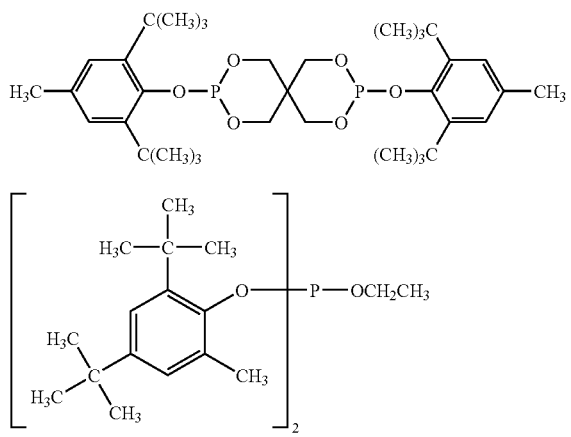
(E)

(F)

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecyinitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydroxylamine derived from hydrogenated tallow amine.

8. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4acet-oxy-3,5-dimethylphenyl)-5,7-di-tert-butyl-benzofuran-2-one, 3-(3,5-dimethyl-4-pivaloyloxy-phenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese, for example CuI.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS# 18600-59-4), and blowing agents.

In general, the compounds of component (b) of the present invention are employed in from about 0.01 to about 5% by weight of the stabilized composition, although this will vary with the particular substrate and application. An advantageous range is from about 0.05 to about 3%, and especially 0.05 to about 1%.

The UVA's of component (b) as well as further optional additives, may be incorporated into the polymeric substrate according to methods known to those skilled in the art.

The UVA's of component (b) and optional further additives may be added to the polymer to be stabilized either separately or together.

The present stabilizers of component (b) of this invention and optional further additives may be applied to or incorporated in the polymeric substrate for example by melt blending, solution blending, solution casting or adsorption from solution.

For example, additives of component (b) and optional further additives may be incorporated in the polymeric substrate before or after molding or also by applying the dissolved or dispersed additive mixture to the polymeric substrate, with or without subsequent evaporation of the solvent. Additives of component (b) and optional further additives can also be added to the polymeric substrate in the form of a masterbatch which contains these components in a concentration of, for example, about 2.5% to about 50% by weight.

For example, the additives of component (b), optional further additives and the polymeric substrate may all be dissolved in a mutually compatible solvent wherein the concentration of polymer in the solvent ranges from about 5 to about 50% by weight of the solvent. The solution may then be dried at an appropriate temperature to produce a cast film containing a blend of polymer and the additive(s).

Alternatively, additive compounds of component (b) and optional further additives are blended into a polymeric substrate by dissolving the additive(s) in a volatile solvent to provide a solution with an additive concentration of about 5 to about 50% by weight. The solution is then mixed with the polymer and the mixture is dried thereby providing polymer particles which are substantially evenly coated with additive(s). The coated polymer particles may then be fed to an extruder wherein the mixture is melt blended and extruded to produce an extrudate containing the polymeric substrate and additive(s).

If in a liquid form, the stabilizers of component (b) may be applied directly to polymer particles by stirring the polymer particles in the liquid additive mixture until the additive mixture is evenly dispersed on the surface of the polymer particles. The polymer may then be fed to an extruder to produce an extrudate of polymer substrate containing the additives.

The compositions of this invention may also be prepared by submitting the stabilizers of component (b), optional further additives and solid polymeric material to an extruder followed by melt blending and extruding the molten mixture. Alternatively, the polymeric material and additives may be melt blended in a thermostatted vessel where the components are in molten form, followed by cooling of the mixture.

Component (b) and optional further additives can also be added before or during the polymerization or before crosslinking.

Component (b) and optional further additives can be incorporated into the polymeric substrate in pure form or encapsulated in waxes, oils or polymers.

Component (b) and optional further additives can also be sprayed or coated onto the polymeric substrate. It may be used to dilute other additives (for example the conventional additives indicated above) or their melts so that it can be sprayed or coated together with these additives onto the polymeric substrate. Addition by spraying during the deactivation of the polymerization catalysts is particularly advantageous, it being possible to carry out spraying using, for example, the steam used for deactivation.

In the case of spherically polymerized polyolefins it may, for example, be advantageous to apply component (b) optionally together with other additives, by spraying.

For instance, component (b) and optional further additives are incorporated into the polymeric substrate of component (a) by melt blending.

The compositions of the present invention can be used in various forms, for example as films, fibers, ribbons, molded materials, profiles or as binders for paints, adhesives or cement.

The following Examples are meant for illustrative purposes only.

SYNTHETIC EXPERIMENTAL PROCEDURES

A) Benzoxazinones

The general synthetic scheme for the preparation of the present benzoxazinone UVA's is as below:

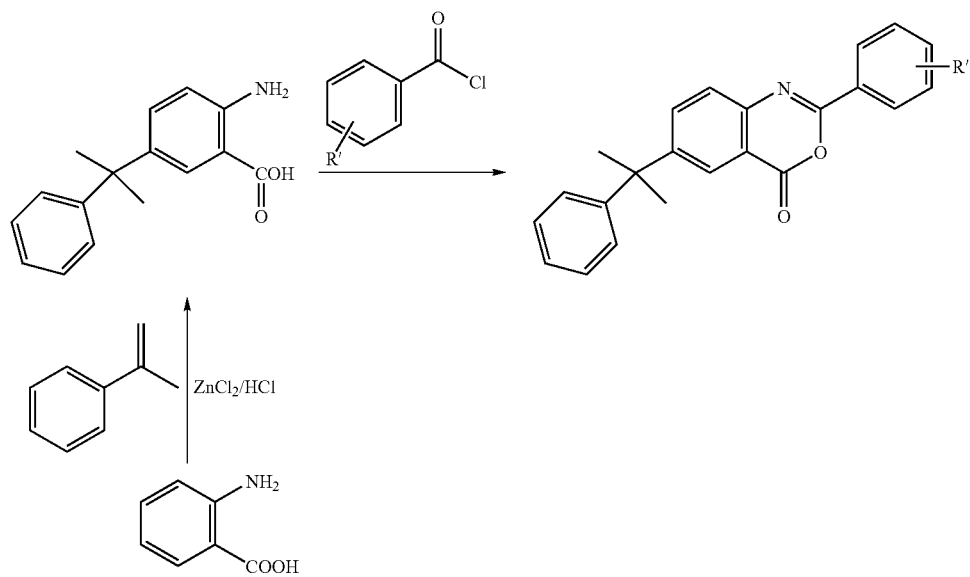

EXAMPLE A1

2-Amino-5-α-cumylbenzoic Acid

A mixture of anthranilic acid (82 g, 0.6 mol), α-methylstyrene (168 mL, 1,28 mol), zinc chloride (82 g, 0.6 mol) and concentrated hydrochloric acid (100 mL) is heated to 120° C. for four hours. The mixture is cooled and diluted with water (100 mL). The pH is adjusted to approximately 4 using 50% sodium hydroxide. The resulting solids are collected, washed with water and then partitioned between methylene chloride and water. The pH is adjusted to 5–6 with dilute hydrochloric acid giving two clear phases. The organic phase is separated and then dried over anhydrous sodium sulfate. The methylene chloride is removed and the solid residue obtained is recrystallized from heptane/toluene giving the title intermediate compound as a white solid melting at 142–144° C.

EXAMPLE A2

2-Amino-5-methoxybenzoic Acid

This compound is prepared according to the procedure described in Organic Preparation and Procedures Int., 13, 189 (1981).

EXAMPLE A3

4-Amino-biphenyl-3-carboxylic Acid

Methyl 4-amino-biphenyl-3-carboxylate is prepared according to the procedure described in WO 99/462,237.

Methyl 4-amino-biphenyl-3-carboxylate (15.2 g, 0.67 mol) is dissolved in ethanol (100 mL) and a solution of sodium hydroxide (3.0 g, 0.75 mol) in 20 mL of water is added. The resulting solution is heated to 50° C. for five hours. The mixture is then cooled and the pH adjusted to about 4 with hydrochloric acid. Some insoluble material is removed by filtration. The filtrate is then diluted with 100 mL of water and the solid formed is collected. The solid is purified by dissolving in dilute sodium hydroxide solution, extraction with ethyl acetate and reacidification to pH 4 with hydrochloric acid. The title intermediate compound is obtained as a light brown solid melting at 208–209° C.

EXAMPLE A4

4-Phenylsulfonylbenzoyl Chloride

Preparation 1 of WO 96/262,196 described the reaction of sodium benzenesulfinate (43 g, 0.26 mol) and 4-fluoroacetophenone (30 g, 0.22 mol) at 130° C. in dimethyl sulfoxide (200 mL) for 48 hours. The mixture is then poured into 1000 mL of water. The solid formed is colled and dried to give 50 g of 1-(4-phenylsulfonyl-phenyl)-ethanone. This solid is suspended in ethanol (350 mL), heated to 60° C. and treated as described in J. Med. Chem., 34, 3295 (1991) to give 4-phenylsulfonyl benzoic acid melting at 269–271° C. A suspension of 4-phenyl sulfonylbenzoic acid (15 g, 0.57 mol) in toluene (50 mL) is treated with thionyl chloride (25 mL). A few drops of N,N-dimethylformamide are added and the suspension is heated to 70° C. for three hours. The solution is concentrated to give the title intermediate compound which is used without further purification.

The following benzoxazin-4-ones are made according to the general procedure described in Example 24 below. The acid chlorides used are commercially available or made by reacting the respective carboxylic acid with thionyl chloride as described in Example 23.

EXAMPLE A5

2-(4-Trifluoromethylphenyl)-6-α-cumyl-4H-3,1-benzoxazin-4-one

To a solution of 2-amino-5-α-cumylbenzoic acid (13.5 g, 0.53 mol, prepared in Example 20) and triethylamine (7.8 g, 0.56 mol) in tetrahydrofuran (200 mL) is added dropwise at room temperature a solution of 4-trifluoromethylbenzoyl chloride (11 g, 0.53 mol). The resulting suspension is stirred at room temperature overnight, then filtered and concentrated to a solid that is then suspended in acetic anhydride and heated to 115° C. for three hours. The resulting solution is cooled and concentrated to an oil. The oil is taken up in ethanol (100 mL) and allowed to stand. The resulting solid formed is coiled and dried to give 15.4 g of the title compound melting at 104–105° C. The structure of the compound is confirmed by $^1$Hnmr (CDCl$_3$) 500 MHz: δ 1.78 (s, 6H); 7.23 (t, 1H); 7.23 (d, 2H); 7.31 (t, 2H); 7.60 (d, 1H); 7.64 (dd, 1H); 7.78 (d, 2H); 8.26 (d, 1H). $^{19}$Fnmr (fluorinated species at −69.57 ppm).

EXAMPLE A6

2-phenyl-6-α-cumyl-4H-3,1-benzoxazin-4-one; melts at 109–111° C.

EXAMPLE A7

2-(3-trifluoromethylphenyl)-6-methoxy-4H-3,1-benzoxazin-4-one; melts at 110–111° C.

EXAMPLE A8

2-(2-trifluoromethylphenyl)-6-methoxy-4H-3,1-benzoxazin-4-one; melts at 98–100° C.

EXAMPLE A9

2-(4-trifluoromethylphenyl)-6-methoxy-4H-3,1-benzoxazin-4-one; melts at 137–138° C.

EXAMPLE A10

2-(4-bromophenyl)-6-methoxy-4H-3,1-benzoxazin-4-one

EXAMPLE A11

2-(4-phenylphenyl)-6-methoxy-4H-3,1-benzoxazin-4-one

EXAMPLE A12

2-(4-phenylsulfonylphenyl)-6-methoxy-4H-3,1-benzoxazin-4-one

EXAMPLE A13

2-(3-trifluoromethylphenyl)-6-α-cumyl-4H-3,1-benzoxazin-4-one; melts at 97–99° C.

EXAMPLE A14

2-(4-methoxyphenyl)-6-α-cumyl-4H-3,1-benzoxazin-4-one; melts at 135–137° C.

EXAMPLE A15

2-(2-methoxyphenyl)-6-α-cumyl-4H-3,1-benzoxazin-4-one; melts at 119–121° C.

EXAMPLE A16

2-(3-methoxyphenyl)-6-α-cumyl-4H-3,1-benzoxazin-4-one; melts at 136–137° C.

EXAMPLE A17

2-(3-methylphenyl)-6-α-cumyl-4H-3,1-benzoxazin-4-one; melts at 164–165° C.

EXAMPLE A18

2-(4-methoxycarbonylphenyl)-6-α-cumyl-4H-3,1-benzoxazin-4-one; melts at 150–152° C.

EXAMPLE A19

2-(3-methoxycarbonylphenyl)-6-α-cumyl-4H-3,1-benzoxazin-4-one; melts at 165–167° C.

EXAMPLE A20

2-(4-phenylsulfonylphenyl)-6-α-cumyl-4H-3,1-benzoxazin-4-one; melts at 148–150° C.; and

EXAMPLE A21

2-(3-trifluoromethylphenyl)-6-phenyl-4H-3,1-benzoxazin-4-one; melts at 154–155° C.

According to the above procedures, the following benzoxazinones are prepared:

EXAMPLE A22

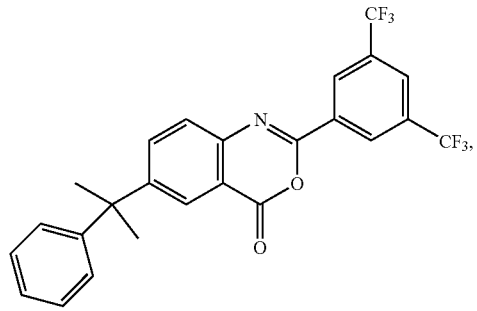

mp 155–156° C

EXAMPLE A23

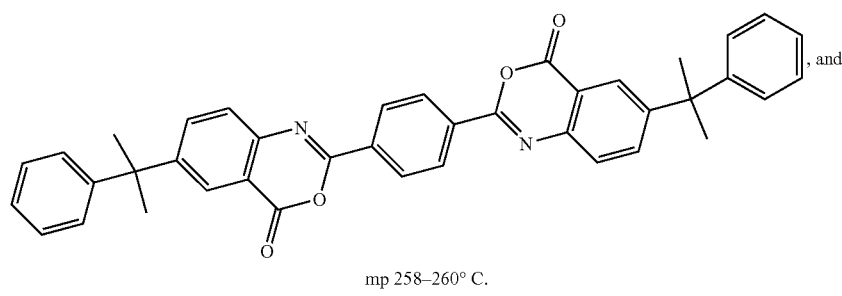

mp 258–260° C.

EXAMPLE A24

2-(2-trifluoromethylphenyl)-6-α-cumyl-4H-3,1-benzoxazin-4-one, consistent with proton NMR

EXAMPLE A25

4-(4-methyphenyl)-6-α-cumyl-4H-3,1-benzoxazin-4-one, consistent with proton NMR

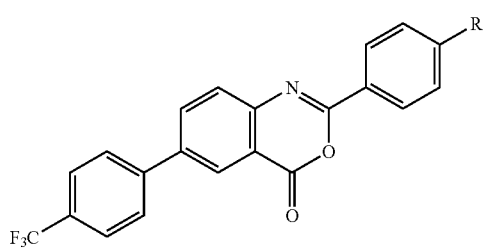

R is $CF_3$ or Phenyl, and

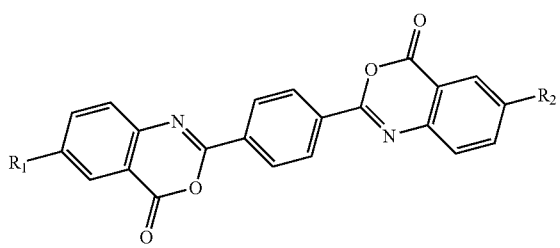

$R_1=R_2=CF_3$
$R_1=$cumyl
$R_2=CF_3$ or phenyl-$CF_3$

Oxanilides are prepared for example according to the following general scheme:

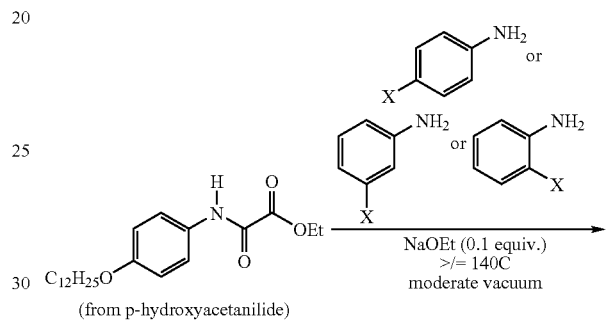

(from p-hydroxyacetanilide)

B) Oxanilides

EXAMPLE B1

N-(4-Dodecyloxyphenyl)oxalamic acid ethyl ester

In a 1 L jacketed flask under a nitrogen atmosphere is added 60 g (0.2425 mols) of p-dodecyloxyaniline, 650 mL of $CH_2Cl_2$ and 56.6 g of pyridine (0.716 mols) and the resulting solution is cooled to 0° C. Maintaining an internal temperature below 5° C., 46.3 g (0.339 mols) of ethyl chlorooxoacetate is then added dropwise over a period of one hour. After the addition is complete, the internal temperature is maintained at 10° C. overnight. To the resultant reaction mixture is added rapidly 400 mL of 1N HCl and the resultant mixture is allowed to warm to RT. The reaction mixture is stirred for one hour than the organic phase separated. The organic phase is dried over anhydrous sodium sulphate and isolubles removed by filtration. The volatiles are removed in vacuo and the residue is recrystallized from ethanol (250 mL). The solid is washed twice with ethanol (50 mL) at 0° C. to give 64.1 g of a white solid, mp. 70.5–72° C. The NMR, MS and IR spectra are consistent with the product.

EXAMPLE B2

N-(4-Dodecyloxyphenyl)-N'-(4-phenyloxyphenyl) oxalamide

A solution of N-(4-dodecyloxyphenyl)oxalamic acid ethyl ester (10 g, 0.026 mol), 4-phenoxyaniline (5 g, 0.026 mol) and lithium t-butoxide (0.2 g, 0.0026 mol) in xylene (50 mL) isheated to gentle reflux. A distillate of ethanol/xylene is slowly collected; the reaction volumn is kept at 50 mL by adding xylene. Heating and distillation continued for 3 hours. The reaction mixture is cooled, the solids are collected and washed sequentially with warm ethyl acetate, ethanol, water and finally ethanol. There is obtained 11.5 g white solid mp: 179–181.

Following the procedures of example 1 and example 2, the following dodecyloxy oxalamides are prepared.

EXAMPLE B3

N-(4-Dodecyloxyphenyl)-N'-(4-methoxyphenyl) oxanilide

Product obtained as a slight greyish solid sinters at 200–205° C. and has a final mp >250° C. Product verified by NMR, MS and IR.

EXAMPLE B4

N-(4-Dodecyloxyphenyl)-N'-(p-toluyl)-oxanilide

Product obtained as a white powder approximately 96% pure by NMR and MS with mp 184–192° C. Product verified by NMR, MS and IR.

EXAMPLE B5

N-(4-cyanophenyl)-N'-(4-Dodecyloxyphenyl)oxanilide

Product obtained as a slight beige powder which sinters at 194–198° C. and has a mp >250° C. Product verified by NMR, MS, and IR. Expected % C: 72.13, % H: 7.85, % N: 9.35; Found: % C: 72.11, % H: 8.17, % N: 8.94.

EXAMPLE B6

N-(4-Dodecyloxyphenyl)-N'-(3-methoxyphenyl) oxanilide

Product obtained as a white powder which sinters at 160–163° C. and has a final mp >250° C. Product verified by NMR, MS, and IR. Expected % C: 71.34, % H: 8.43, % N: 6.16; Found: % C: 70.93, % H: 8.26, % N: 5.78.

EXAMPLE B7

N-(4-Dodecyloxyphenyl)-N'-(3-toluyl)oxanidide

Product obtained as a white powder with mp 139–141° C. Product verified by NMR, MS and IR.

EXAMPLE B8

N-(3-cyanophenyl)-N'-(4-Dodecyloxyphenyl)oxanilide

Product obtained as a white powder with mp 165–168° C. Product Verified by NMR, MS, and IR.

EXAMPLE B9

N-(4-Dodecyloxyphenyl)-N'-(3-trifluoromethylphenyl)-oxanilide

Product obtained as a white solid with mp 143–145° C.: Product verified by NMR, MS and IR. Expected % C: 65.84, % H: 7.16, % N: 5.69; Found: % C: 65.80, % H: 6.82, % N: 5.72

EXAMPLE B10

N-(4-Dodecyloxyphenyl)-N'(4'-trifluoromethyl-1,1'-biphen-4-yl)-oxanilide

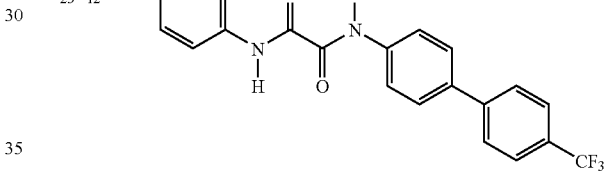

The title oxanilide is prepared from N-(4-bromophenyl)-N'-(4-Dodecyloxyphenyl)oxanilide, 4-trifluoromethylphenylboronic acid, palladium(II) diacetate, triphenylphosphine, 3 mL of 2M sodium carbonate, 5 mL of water, and 200 mL of 1-propanol. MS m/z 568.

EXAMPLE B11

N-[4-(2-Ethylhexyloxy)phenyl]-N'-(3'-trifluoromethyl-1,1'-biphen-4-yl)-oxanilide

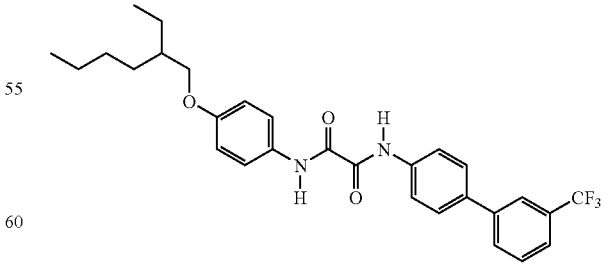

4-Amino-3'-trifluoromethyl-1,1'-biphenyl: To a mixture of 3.44 g (0.02 mol) of 4-bromoaniline and 4.50 g (0.024 mol) of 3-trifluoromethylphenylboronic acid in 200 mL of 1-propanol that is evacuated and filled with nitrogen (3×) is added sequentially 0.18 grams (0.8 mmol) of palladium(II) acetate, 0.630 (2.4 mmol) of triphenylphosphine, 12 mL of 2M aqueous sodium carbonate, and 10 mL of distilled water. The reaction mixture is evacuated and filled with nitrogen (3×) and then stirred for 10 minutes. The reaction mixture is heated at 76° C. for 5.5 hours. The solvent is removed in vacuo and the residue purified sequentially by dry-column chromatography (7:3 toluene:ethyl acetate eluent) and dry-column flash chromatography (toluene eluent) to give 2.38 grams of a light amber liquid. Flow injection LC/AP$_c$/MS m/z 238 (M+H).

A mixture of 2.17 g (9.1 mmol) of 4-amino-3'-trifluoromethyl-1,1'-biphenyl, 3.21 g (10 mmol) of N-[4-(2-ethylhexyloxy)phenyl]oxalamic acid ethyl ester, 0.8 g (1 mmol) of lithium tert-butoxide in 45 mL of m-xylene is heated at reflux for 8 hours. The reaction mixture is cooled an the solid collected by filtration. The solid is purified by recrystallization from toluene and then triturated with acetonitrile to give 1.39 grams (30%) of a white solid mp 143–146° C. MS: m/z 512; UV (ethyl acetate) lambda max 298 (molar extinction 26,408). Anal. Calcd for $C_{29}H_{31}F_3N_2O_3$: C, 67.96; H, 6.10; N, 5.47. Found: C, 67.49; H, 6.30; N, 5.43.

N-[4-(2-Ethylhexyloxy)phenyloxalamic acid ethyl ester 4-(2-ethylhexyoxy)aniline is prepared according to the procedure described in U.S. Pat. No. 5,484,696. The oxalamic acid ethyl ester is prepared according to the procedure described in Example 1. Product confirmed by NMR.

EXAMPLE B12

N-[2-(2-Ethylhexyloxy)phenyl]-N'-(3'-trifluoromethyl-1,1'-biphen-4-yl)-oxanilide

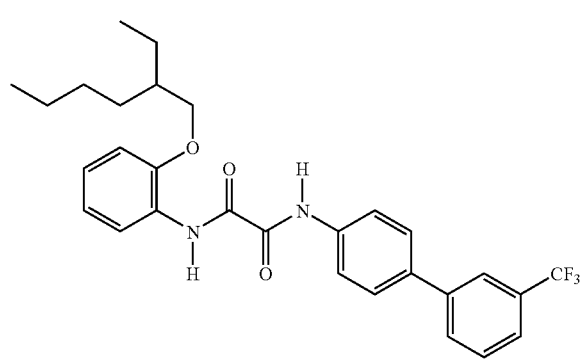

The procedure of example 11 is repeated using N-[2-(2-ethylhexyloxy)phenyl]oxalamic acid ethyl ester in place of N-[4-(2-ethylhexyloxy)phenyl]oxalamic acid ethyl ester.

EXAMPLE B13

4-Dodecyloxy-4'-trifluoromethyloxanilide

This compound is made according to the general procedures as described above. The product sinters in a melting tube as 225–231° C. and melts >250° C. Structure confirmed by $^1$H NMR, MS and IR.

C) Benzylidene Malonates

Benzylidene malonates are prepared according to the following general procedure:

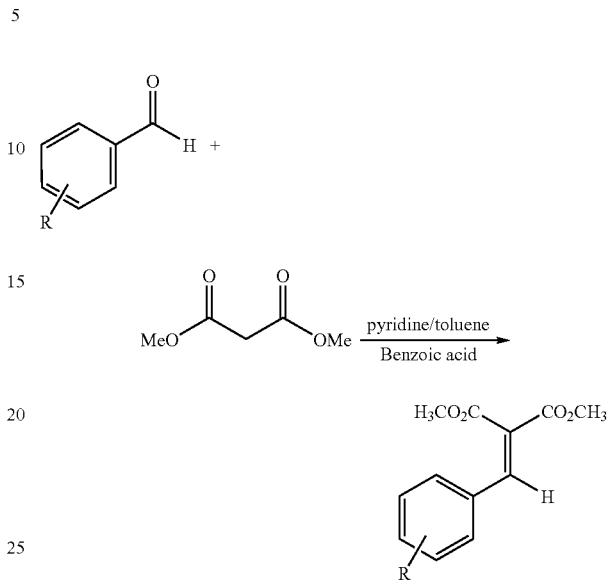

The general synthetic scheme involves reaction of an appropriately substituted benzoic acid with dimethyl malonate in the present of pyridine and toluene.

The compounds prepared are substituted on the benzylidene ring in the ortho, meta and para positions by an electron withdrawing (EW) trifluoromethyl groups and by electron donating (ED) groups methyl, phenyloxy and methoxy.

Photographic studies indicate that substitution that photopermanence can be substantially improved by substitution of the two ortho positions by methoxy moieties.

Early work in poly(methyl methacrylate) indicate that these compounds are very stable.

Some eight benzylidenemalonate compounds are prepared using the general procedure given below. The structures of each of the compounds is confirmed by $^1$Hnmr analysis.

EXAMPLE C1

Dimethyl 2,4-Dimethoxybenzylidenemalonate 2,4-Dimethoxybenzaldehyde (10.0 g, 0.060 mol), dimethyl malonate (9.5 g, 0.072 mol), piperidine (1.5 g, 0.017 mol), benzoic acid (1.8 g, 0.015 mol) and 100 mL of toluene are stirred at reflux for 5.5 hours under a Dean Stark trap to remove water. After cooling to room temperature, the reaction mixture is partitioned between ethyl acetate and water. The organic layer is washed with 10% hydrochloric acid, water and brine. The resulting solution is dried over anhydrous magnesium sulfate and then concentrated to yield 17.8 g of an orange syrup which is purified by chromatography on silica gel (2:1, heptane:ethyl acetate) to provide 12.8 g of the title compound as a pale yellow solid melting at 71–73° C.

EXAMPLE C2

Dimethyl 2,4,6-Trimethoxybenzylidenemalonate

Following the procedure given above, 9.8 g of the title compound is prepared from 2,4,6-trimethoxybenzaldehyde as a white solid melting at 123–125° C. after recrystallization from heptane/ethyl acetate.

EXAMPLE C3

Dimethyl 2,4,6-Trimethylbenzylidenemalonate

Following the procedure given above, 9.6 g of the title compound is prepared from 2,4,6-trimethylbenzaldehyde as a pale yellow oil after purification by chromatography on silica gel (15:1, heptane:ethyl acetate).

EXAMPLE C4

Dimethyl 4-Trifluoromethylbenzylidenemalonate

Following the procedure given above, 5.5 g of the title compound is prepared from 4-trifluoromethylbenzaldehyde as a white solid melting at 49–50° C. after recrystallization from heptane/ethyl acetate.

EXAMPLE C5

Dimethyl 3-Trifluoromethylbenzylidenemalonate

Following the procedure given above, 6.2 g of the title compound is prepared from 3-trifluoromethylbenzaldehyde as a white solid melting at 53–54° C. after recrystallization from heptane/ethyl acetate.

EXAMPLE C6

Dimethyl 4-Phenoxybenzylidenemalonate

Following the procedure given above, 9.8 g of the title compound is prepared from 4-phenoxybenzaldehyde as a yellow syrup.

EXAMPLE C7

Dimethyl 2-Methoxy-1-naphthylidenemalonate

Following the procedure given above, 9.3 g of the title compound is prepared from 2-methoxy-1-naphthaldehydeas a yellow solid melting at 78–81° C. after purificiation by chromatography on silica gel (3:1, heptane:ethyl acetate).

EXAMPLE C8

Dimethyl 2,2-Diphenylethylidenemalonate

This compound is made by the procedure of N. J. Head, G. A. Olah and G. K. Surya Prakash, J. Am. Chem. Soc., 117, 11205 (1995).

To a stirred solution of titanium tetrachloride (22 mL, 0.2 mol), carbon tetrachloride (50 mL) and tetrahydrofuran (400 mL) at 0° C. is added benzophenone (18.2 g, 0.1 mol) and dimethyl malonate (13.3 g, 0.1 mol). After stirring at 0° C. for forty minutes, a solution of pyridine (32 mL) in tetrahydrofuran (70 mL) is added dropwise. The mixture is allowed to warm to room temperature and is then stirred for four days. The formation of a heavy precipitate requires the addition of more tetrahydrofuran to facilitate stirring. Water (100 mL) and ethyl acetate (100 mL) are then added. The mixtures separates into two layers. The aqueous layer is extracted with additional ethyl acetate. The combined organic layers are washed with brine, sodium bicarbonate and more brine. The solution is then dried over anhydrous magnesium sulfate and concentrated. The crude material is a white semi-solid slurry which is then recrystallized twice from heptane/ethyl acetate to afford 11.3 g of the title compound as a white solid melting at 120–122° C.

D) Quinazolines

The general synthetic scheme involves reacting 2,4-dihydroxyisoquinaoxaline with phosphorus oxychloride, a tert-amine at 130° C., then with aluminum chloride, and resorcinol in sulfolane at 60° C. to give an intermediate substituted by a chloro group on the ring containing the two N-atoms. The intermediate with the chloro group or with the free hydroxyl group on the phenyl ring can they be used to prepare novel UV absorbers containing either ED or EW moieties.

Quinazolines are prepared for example according to the following general procedures:

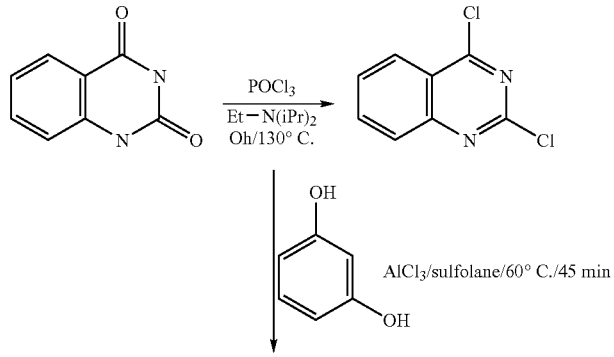

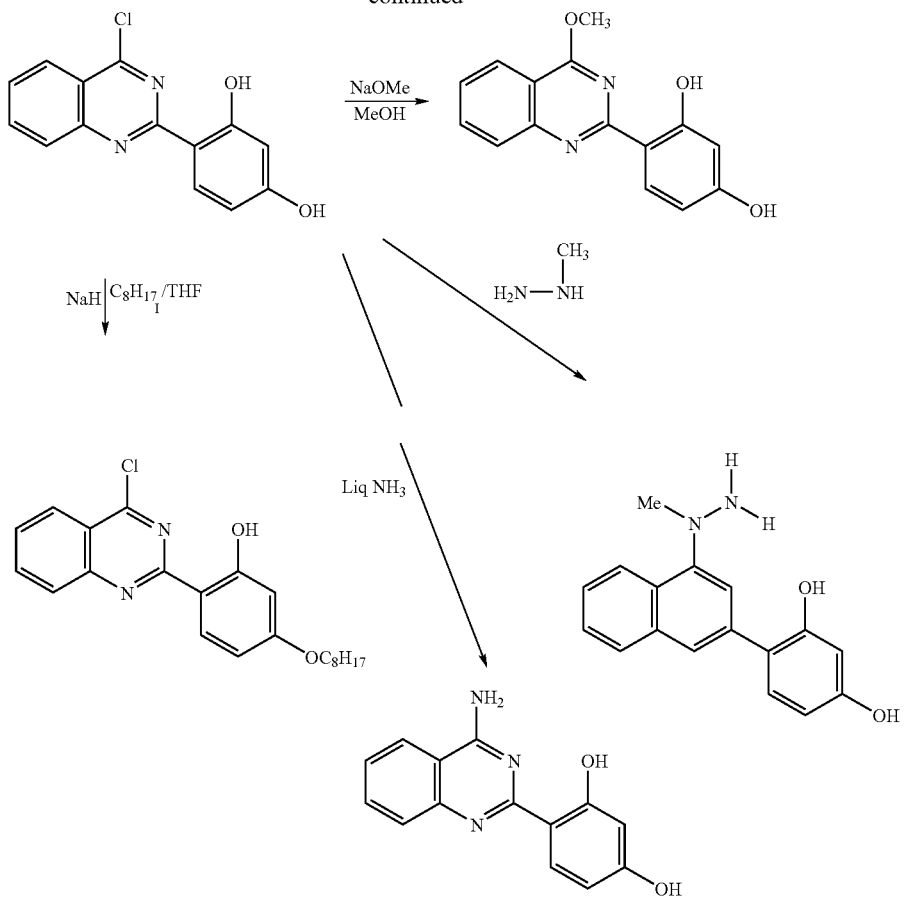

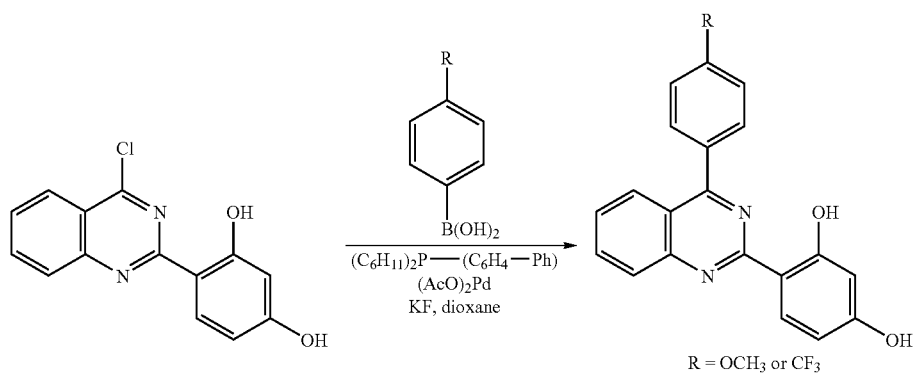

E) Benzotriazoles

General synthetic procedures for benzotriazole ring construction are located in U.S. Pat. Nos. 5,977,219 and 6,166,218, the disclosures of which are hereby incorporated by reference. To ensure compounds of high purity are tested, all final products are chromatographed on silica gel and sublimed except the compound of Example 3 which is chromatographed twice on silica gel.

EXAMPLE E1

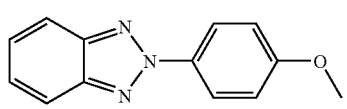

Isolated as a white solid; melting point=111–112° C.; $^1$HNMR (500 MHz, CDCl$_3$): δ=8.29 (m, 2H), 7.93 (m, 2H), 7.42 (m, 2H), 7.07 (m, 2H), 3.91 (s, 3H); MS m/z: 225, 210, 182. Anal. Calcd. for $C_{13}H_{11}N_3O$: C, 69.32; H, 4.92; N, 18.65. Found: C, 69.10; H, 4.80; N, 18.65.

EXAMPLE E2

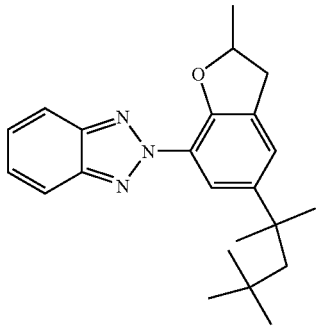

The synthesis of this compound followed the same synthetic conditions used for Example 3. Isolated as a white solid; melting point=128–128.5° C.; $^1$HNMR (300 MHz, $CDCl_3$): δ=8.00 (m, 2H), 7.85 (s, 1H), 7.42 (m, 2H), 7.30 (s, 1H), 5.22 (m, 1H), 3.43 (dd, 1H), 2.93 (dd, 1H), 1.76 (s, 2H), 1.56 (s, 3H), 1.42 (s, 6H), 0.80 (s, 9H). MS m/z: 364 (M+H). Anal. Calcd. for $C_{23}H_{29}N_3O$: C, 76.00; H, 8.04; N, 11.56. Found: C, 75.94; H, 7.98; N, 11.42.

EXAMPLE E3

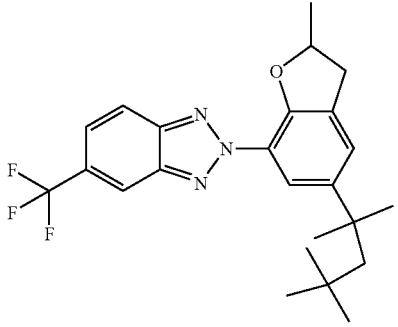

5-Trifluoromethyl-2-(2-hydroxy-5-tert-octylphenyl)-2H-benzotriazole (13.01 g, 0.033 mol), potassium hydroxide (2.37 g, 0.036 mol) and ethanol (60 mL) are charged to a lab reactor and stirred at ambient temperature for two hours. Allyl bromide (4.84 g, 0.039 mol) and potassium iodide (0.34 g, 0.002 mol) are added to the reaction mixture which is heated to 85° C. After holding at 85° C. for 4.5 hours, the solvent is removed and replaced with 100 mL of heptane. The mixture is washed thrice with 40 mL of water. The solvent is then removed to yield 14.2 g of the corresponding O-allyl ether as an off-white solid. $^1$HNMR (300 MHz, $CDCl_3$): δ=8.35 (s, 1H), 8.20–8.12 (d, 1H), 7.67–7.61 (m, 2H), 7.54–7.49 (dd, 1H), 7.11–7.06 (d, 1H), 6.00–5.86 (m, 1H), 5.34–5.16 (m, 2H), 4.65–4.60 (d, 2H), 1.77 (s, 1H), 1.41 (s, 6H), 0.78 (s, 9H).

The O-allyl compound (14.2 g) as prepared above is charged to a reactor and heated to 190–195° C. and held at that temperature for five hours. Flash column chromatography with silica gel and ethyl acetate/heptane solvent as the eluent yielded the allyl-substituted benzotriazole compound (12.2 g) as a yellow oil. MS m/z: 432 (M+H); $^1$HNMR (300 MHz, $CDCl_3$): δ=11.17 (s, 1H), 8.35–8.29 (m, 2H), 8.12–8.05 (d, 1H), 7.72–7.66 (dd, 1H), 7.34–7.29 (d, 1H), 6.18–6.02 (m, 1H), 5.20–5.06 (m, 2H), 3.64–3.53 (d, 2H), 1.81 (s, 2H), 1.46 (s, 6H), 0.78 (s, 9H).

5-Trifluoromethyl-2-(2-hydroxy-3-allyl-5-tert-octyl-phenyl)-2H-benzotriazole (12.16 g, 0.028 mole), methanesulfonic acid (3.34 g, 0.034 mole) and chlorobenzene (50 mL) are charged to a reaction flask fitted with the necessary auxiliary equipment. The reaction mixture is heated to 140C and held there for three hours. After removal of solvent, the brown oil is chromatographed on silica gel using 19:1 hexane/ethyl acetate as the eluent. After second silica gel chromatography, the desired product is obtained as a yellow viscous resin. $^1$HNMR (300 MHz, $CDCl_3$): δ=8.36 (s, 1H), 8.12 (d, 1H), 7.87 (s, 1H), 7.60 (d, 1H), 7.35 (s, 1H), 5.21 (m, 1H), 3.47 (dd, 1H), 2.94 (dd, 1H), 1.79 (s, 2H), 1.57 (d, 3H), 1.44 (s, 6H), 0.8 (s, 9H); MS m/z: 432 (M+H). Anal. Calcd. for $C_{24}H_{28}F_3N_3O$: C, 66.81; H, 6.54; N, 9.74. Found: C, 66.10; H, 6.25; N, 9.76.

EXAMPLE E4

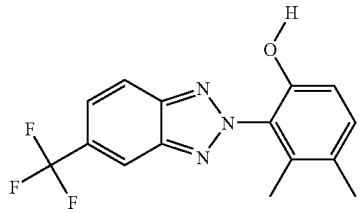

Isolated as a light yellow solid; melting point=127.5–128.5° C.; $^1$HNMR (300 MHz, $CDCl_3$): δ=8.38 (s, 1H), 8.15 (d, 1H), 7.71 (s, 1H), 7.68 (dd, 1H), 7.25 (d, 1H), 6.96 (d, 1H), 2.35 (s, 3H), 2.27 (s, 3H). MS m/z: 308 (M+H). Anal. Calcd. for $C_{15}H_{12}F_3N_3O$: C, 58.63; H, 3.94; N, 13.67. Found: C, 58.66; H, 3.71; N, 13.60.

EXAMPLE D5

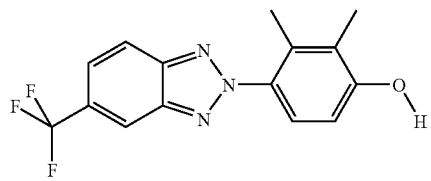

Isolated as a white solid; melting point=135–136° C.; $^1$HNMR (500 MHz, $CDCl_3$): δ=8.33 (d, 1H), 8.09 (d, 1H), 7.65 (d, 1H), 7.31 (d, 1H), 6.78 (d, 1H), 5.30 (broad s, 1H), 2.29 (s, 3H), 2.14 (s, 3H). $^{19}$FNMR (300 MHz, $CDCl_3$, $CF_3COOH$ @ −70 ppm)): −68.9 ppm. Anal. Calcd. for $C_{15}H_{12}F_3N_3O$: C, 58.63; H, 3.94; N, 13.67. Found: C, 58.53; H, 3.88; N, 13.72.

EXAMPLE E6

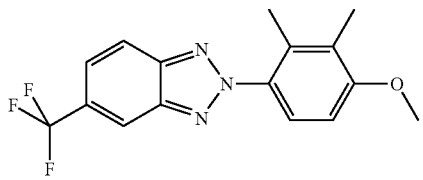

Isolated as a white solid; melting point=109–111° C.; ¹HNMR (300 MHz, CDCl₃): δ=8.34 (s, 1H), 8.10 (d, 1H), 7.63 (dd, 1H), 7.42 (d, 1H), 6.88 (d, 1H), 3.92 (s, 3H), 2.27 (s, 3H), 2.15 (s, 3H). MS m/z: 322 (M+H). Anal. Calcd. for $C_{16}H_{14}F_3N_3O$: C, 59.81; H, 4.39; N, 13.08. Found: C, 59.65; H, 4.10; N, 13.08.

EXAMPLE E7

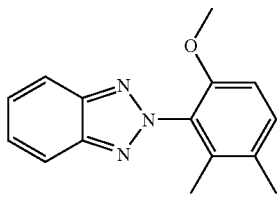

Isolated as a white solid; melting point=121.5–122.5° C.; ¹HNMR (300 MHz, CDCl₃): δ=8.00 (m, 2H), 7.44 (m, 2H), 7.30 (d, 1H), 6.84 (d, 1H), 3.72 (s, 3H), 2.30 (s, 3H), 1.81 (s, 3H). MS m/z: 254 (M+H). Anal. Calcd. for $C_{15}H_{15}N_3O$: C, 71.13; H, 5.97; N, 16.59. Found: C, 71.01; H, 5.82; N, 16.75.

EXAMPLE E8

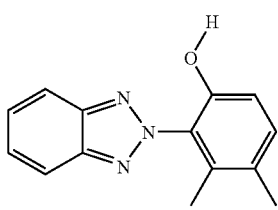

Isolated as a white solid; melting point=166.5–167.5° C.; ¹HNMR (300 MHz, CDCl₃): δ=8.04 (s, 1H), 8.00 (m, 2H), 7.51 (m, 2H), 7.21 (d, 1H), 6.95 (d, 1H), 2.34 (s, 3H), 2.32 (s, 3H); MS m/z: 240 (M+H). Anal. Calcd. for $C_{14}H_{13}N_3O$: C, 70.28; H, 5.48; N, 17.56. Found: C, 70.02; H, 5.58; N, 17.53.

EXAMPLE E9

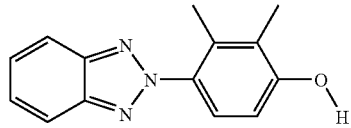

Isolated as a light yellow solid; melting point=189–190° C.; ¹HNMR (300 MHz, CDCl₃): δ=7.94 (m, 2H), 7.46 (m, 2H), 7.30 (d, 1H), 6.78 (d, 1H), 5.19 (s, 1H), 2.28 (s, 3H), 2.14 (s, 3H). MS m/z: 240 (M+H). Anal. Calcd. for $C_{14}H_{13}N_3O$: C, 70.28; H, 5.48; N, 17.56. Found: C, 70.06; H, 5.51; N, 17.65.

EXAMPLE E10

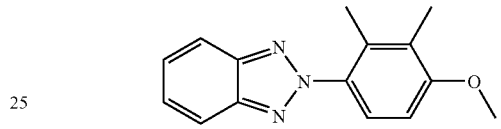

Isolated as a white solid; melting point=110–110.5° C.; ¹HNMR (300 MHz, CDCl₃): δ=7.94 (m, 2H), 7.44 (m, 2H), 7.41 (d, 1H), 6.85 (d, 1H), 3.91 (s, 3H), 2.28 (s, 3H), 2.14 (s, 3H); MS m/z: 254 (M+H). Anal. Calcd. for $C_{15}H_{15}N_3O$: C, 71.13; H, 5.97; N, 16.59. Found: C, 71.03; H, 5.81; N, 16.69.

EXAMPLE E11

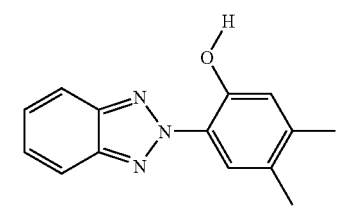

Isolated as a white solid; melting point=143–143.5° C.; ¹HNMR (300 MHz, CDCl₃): δ=11.04 (s, 1H), 8.14 (s, 1H), 7.95 (m, 2H), 7.46 (m, 2H), 7.01 (s, 1H), 2.32 (s, 3H), 2.31 (s, 3H). MS m/z: 240 (M+H). Anal. Calcd. for $C_{14}H_{13}N_3O$: C, 70.28; H, 5.48; N, 17.56. Found: C, 69.98; H, 5.40; N, 17.63.

EXAMPLE E12

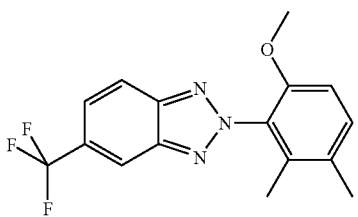

Isolated as a light yellow solid; ¹HNMR (300 MHz, CDCl₃): δ=8.36 (s, 1H), 8.11 (d, 1H), 7.65 (dd, 1H), 7.35 (d, 1H), 6.86 (d, 1H), 3.72 (s, 3H), 2.31 (s, 3H), 1.81 (s, 3H). MS m/z: 322 (M+H). Anal. Calcd. for $C_{16}H_{14}F_3N_3O$: C, 59.81; H, 4.39; N, 13.08. Found: C, 59.58; H, 4.03; N, 13.11.
EXAMPLE E13
According to the general procedures as herein described, the following benzotriazoles are prepared:
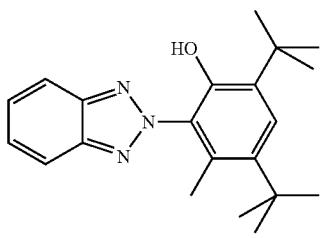
mp 188–189° C.
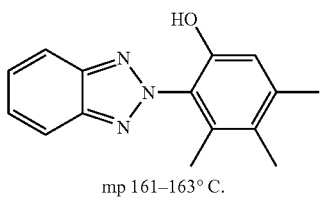
mp 161–163° C.
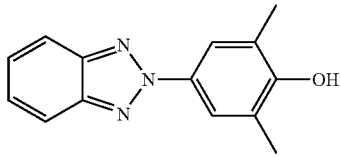
mp 191–193° C.
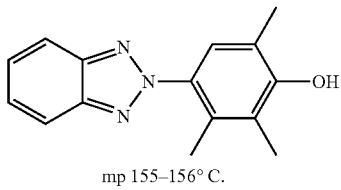
mp 155–156° C.
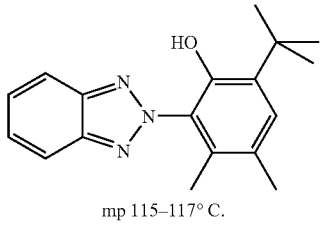
mp 115–117° C.
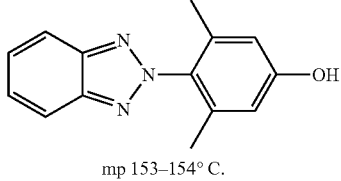
mp 153–154° C.
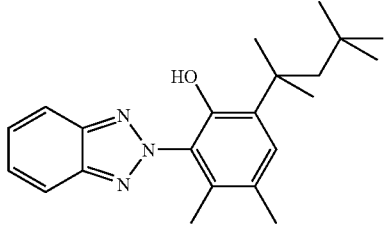
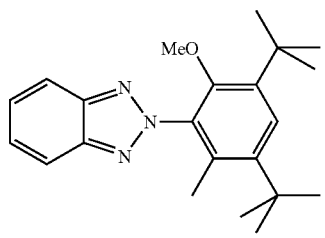
mp 142–143° C.
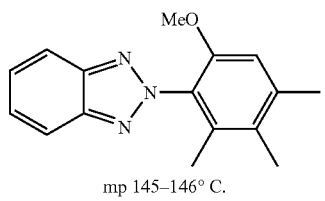
mp 145–146° C.
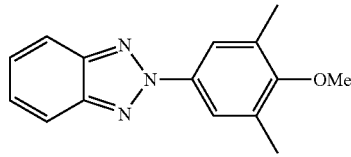
mp 92–94° C.
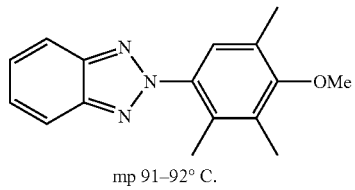
mp 91–92° C.
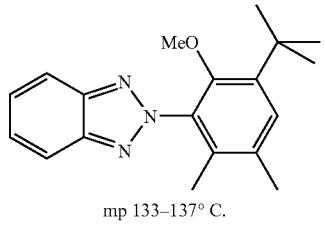
mp 133–137° C.
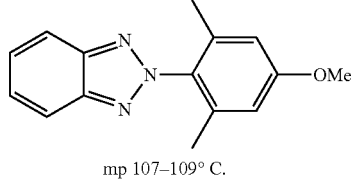
mp 107–109° C.
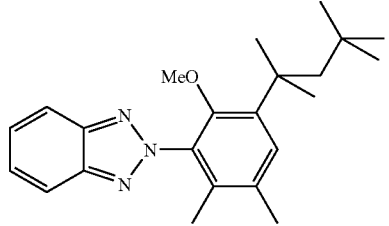

F) Application Examples

Application Example F1: Benzoxazinones

The following compounds are employed in the working Examples:

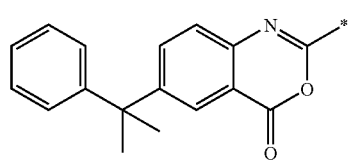

| compound | R₂ | R₃ | R₄ | preparation example |
|---|---|---|---|---|
| 118 | H | H | CF₃ | A5 |
| 119 | H | H | OCH₃ | A14 |
| 176 | OCH₃ | H | H | A15 |
| 109 | H | OCH₃ | H | A16 |
| 108 | H | CH₃ | H | A17 |
| 116 | H | CF₃ | H | A13 |
| 174 | CF₃ | H | H | A24 |
| 120 | H | H | CH₃ | A25 |
| 110 | H | H | COOMe | A18 |
| dicumyl | H | H | (structure shown) | A23 |

The photostabilty of representative benzoxazinones is determined by incorporation into solution and polymer films and monitoring the loss after exposure to UV radiation. Loss is measured by UV absorption.

Solution

The selected benzoxazinones are dissolved in ethyl acetate at the given dilutions and the initial UV spectrum obtained. A portion of the solutions are transferred into borosilicate vials with teflon coated caps and photolyzed in a Rayonet Photochemical Reactor (The Southern New England Ultraviolet Company) fitted with 4 300 nm lamps and 12 350 nm lamps. To ensure equal exposure for all samples the vials are mounted on a merry-go-round unit which revolved at 5 RPM. At selected intervals the samples are removed and the loss of compound is obtained by measuring the loss of UV absorption at the benzoxazinone lambda max. Such loss rates are typically independent of concentration for samples with UV absorbances of greater than 0.8 (Iyengar, R., Schellenberg, B., *Polym. Degrad. Stab.*, 61, 151 (1998), Pickett, J. E., *Macromol. Symp.*, 115, 127 (1997), Pickett, J. E., Moore, J. E, *Die Angew. Makromol. Chem.*, 232, 229 (1995).) Results are in the table below.

| compound | g/100 mL | Abs max | Absorbance 0 h | 18 h | 42 h | ΔA | ΔA/100 h |
|---|---|---|---|---|---|---|---|
| 118 | 2.2 | 305 nm | 1.81 | 1.79 | 1.77 | 0.04 | 0.10 |
| 119 | 3.3 | 308 nm | 1.65 | 1.56 | 1.44 | 0.21 | 0.50 |
| dicumyl | 2.1 | 354 nm | 1.57 | 1.51 | 1.43 | 0.14 | 0.33 |
| ME | 2.2 | 300 nm | 1.73 | 1.53 | 1.06 | 0.67 | 1.59 |

ΔA is the loss of absorption at lambda max for the overall exposure time.
ΔA/100 h is the loss rate expressed in terms abs units per 100 hours.

Similar results are obtained in cyclohexane

The compound substituted with the CF₃ electron withdrawing group is shown to be extremely photostable in polar and non-polar solvents.

The enhanced photostability of the compounds of this invention are confirmed in polymeric compositions.

Polycarbonate Films

PC (polycarbonate) films, 1 mil thick, are cast from room temperature methylene chloride solutions of polycarbonate flake (Lexan® 145, GE Plastics) and between 1 and 3% benzoxazinone derivative (wt % based on polycarbonate) using a calibrated drawdown bar. The free standing films are mounted in cardboard holders, secured in metal frames and exposed in an Atlas Ci65 xenon arc weatherometer under dry conditions (ASTM G26). Loss of UVA is determined by monitoring loss of absorbance at 345 nm. This wavelength is selected to minimize the impact of polycabonate degradation products which absorb in the UV. Results are below.

|          | Absorbance |       |       |       |      |        |
| -------- | ---------- | ----- | ----- | ----- | ---- | ------ |
| compound | 0 h        | 250 h | 500 h | 750 h | ΔA   | ΔA/100 h |
| 119 (2.08%) | 3.02    | 2.21  | 2.00  | 1.65  | 1.37 | 1.8/h  |
| 118 (2.29%) | 1.95    | 1.95  | 1.95  | 1.95  |      | unchanged |

After 750 hours the PC decomposition products began to skew the UV absorption results.

Polymethyl(methacrylate) Films

Polymethyl (methacrylate) films, 1 mil thick, are cast from room temperature methylene chloride solutions of polymethyl (methacrylate), medium molecular weight, Aldrich and between 1 and 3% benzoxazinone derivative (wt % based on polymer) using a calibrated drawdown bar. The free standing films are mounted in cardboard holders, secured in metal frames and exposed in an Atlas Ci65 xenon arc weatherometer under dry conditions (ASTM G26). Loss of UVA is determined by monitoring loss of absorbance at the maximum nearest 300 nm (ΔA). Due to excessive noise in the UV spectra at 0 hours, data on rate loss is tabulated for most samples beginning at 250 hours of exposure, after a smooth loss rate is observed to eliminate scatter. Results are below.

|          | Absorbance |       |       |       |        |        |        |
| -------- | ---------- | ----- | ----- | ----- | ------ | ------ | ------ |
| compound | 0 h        | 250 h | 500 h | 750 h | 1000 h | 1500 h | 2000 h |
| 176 (2.08%, 300 nm) | 2.7 | 0.5 | — | — | — | — | — |
| 109 (2.08%, 304 nm) | —   | 2.47 | 2.18 | 1.78 | 1.43 | — | — |
| 108 (1.99%, 304 nm) | —   | 3.03 | 2.80 | 2.38 | 2.11 | — | — |
| 116 (2.29%, 305 nm) | —   | 3.33 | 3.25 | 2.92 | 2.67 | 2.43 | 2.17 |
| 174 (2.29%, 280 nm) | —   | 3.07 | 3.02 | 2.77 | 2.64 | 2.43 | 2.22 |

Average loss per 100 h, 250–1000 hours exposure (ΔA @ 1000 h/7.5):

Compound
109:1.04/7.5=0.14
108:0.92/7.5=0.12
116:0.66/7.5=0.09
174:0.43/7.5=0.06

The compounds of the instant invention are more stable in PC and PMMA than similar compounds bearing alternate substitution patterns.

Photographic Compositions

A gelatin coat of the following composition (per m$^2$) is applied in the customary manner to a polyester base.

| Components | Amount |
| ---------- | ------ |
| Gelatin    | 1200 mg |
| Tricresyl Phosphate | 510 mg |
| Hardener*  | 40 mg |
| Wetting Agent** | 100 mg |
| Test UV Absorber | 400 mg |

*potassium salt of 2-hydroxy-4,6-dichloro-s-triazine
**sodium 4,8-diisobutylnaphthalene-2-sulfonate The gelatin coats are dried at 20° C. for seven days.

When the instant UV absorbers are used, clear transparent coats are obtained which are suitable for photographic recording material for example as a UV filter coat.

The benzoxazinones of this invention are more permanent than others upon exposure to 60 KJ of UV photography as measured by loss of optical density:

|          | % change in OD |       |
| -------- | -------------- | ----- |
| compound | 30 KJ          | 60 KJ |
| 120      | 13             | 60    |
| 110      | 17             | 40    |
| 118      | 8              | 12    |
| 116      | 5              | 6     |

Polycarbonate Films

Polycarbonate films of about 1 mil thickness and containing a UV absorber are prepared by dissolving polycarbonate granules (LEXAN® 145, General Electric) and UV absorbers in methylene chloride and casting the films on a glass plate using a drawdown bar. The films are exposed for 250 hours in a Xenon arc Weather-Ometer according to ASTM G26 test method and the color change (delta YI) versus that for unexposed films are recorded below. The color measurements (yellowness index—YI) are carried out on an ACS spectrophotometer, small area view, spectral component included d/8, D65, 10° observer, YI 1925 for unexposed and exposed samples.

|                       | Delta YI |           |
| --------------------- | -------- | --------- |
| Additive (weight percent) | 1000 hours | 2000 hours |
| Blank (no stabilizer) | 14.9     | 20.5      |
| Tinuvin ® 234 (2.50%) | 2.6      | 7.6       |
| Compound 118 (2.29%)  | 4.5      | 9.2       |
| Compound 119 (2.08%)  | 15.8     | 20.1      |

Tinuvin ® 234 is 2-(2-hydroxy-3,5-di-α-cumylphenyl)-2H-benzotriazole.

These data show that the instant compounds are efficacious when used in thermoplastic compositions, as evidenced in low delta YI measurements.

Application Example F2: Malonates

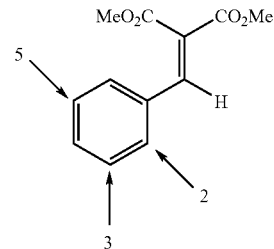

The following table illustrates a desireable red shift of di and tri methoxy substituted benzylidene malonates substituted at the 2-position vs. those substituted at the 3-position:

| methoxy postition | λmax |
|---|---|
| 2, 4 | 332 |
| 2, 3 | 283 |
| 3, 4 | 327 |
| 2, 4, 6 | 326 |
| 3, 4, 5 | 313 |

A red shift is generally desireable for UV absorbers and results in a broader spectral coverage.

Other positions are unsubstituted (hydrogen).

Solution

Ethyl Acetate solutions of various benzylidene malonate derivatives, ~20 mg/L, are exposed as in Application Example 1 to determine the relative photopermanence. Loss of compound is monitored by loss of absorbance at lambda max. Results are below.

Series A

| | Absorbance | | | | | |
|---|---|---|---|---|---|---|
| Compound | 0 h | 6 h | 12 h | 18 h | ΔA | ΔA/100 |
| 104 (331 nm) | 1.75 | 1.72 | 1.65 | 1.55 | 0.20 | 1.11 |
| 141 (325 nm) | 1.32 | 1.25 | 1.15 | 1.07 | 0.27 | 1.50 |

Compound 104 is shown to be more stable than 141 in Ethyl Acetate solution.

Series B

| | Absorbance | | | | | | |
|---|---|---|---|---|---|---|---|
| Compound | 0 h | 6 h | 12 h | 18 h | 30 h | ΔA | ΔA/100 |
| 141 (325 nm) | 1.18 | 1.07 | 0.93 | 0.84 | 0.70 | 0.48 | 1.60 |
| 3,4,5-tri (315 nm) | 1.00 | 0.87 | 0.69 | 0.51 | 0.15 | 0.85 | 2.83 |
| PR25 (310 nm) | 1.94 | 1.87 | 1.80 | 1.72 | 1.57 | 0.37 | 1.23 |
| 3-mono (278 nm) | 2.20 | 1.95 | 1.83 | 1.70 | 1.48 | 0.72 | 2.40 |
| 2,3-di (283 nm) | 1.81 | 1.72 | 1.63 | 1.55 | 1.39 | 0.42 | 1.40 |
| 3,4-di (327 nm) | 1.80 | 1.74 | 1.63 | 1.58 | 1.41 | 0.37 | 1.23 |

The trimethoxy compound 141 of this invention is more red shifted and more stable in ethyl acetate solution than the trimethoxy compound of U.S. Pat. No. 5,882,624.

The 3,4,5-tri compound is not as stable as the 2,4,6-tri compound (compound 141). An indirect comparison shows that the 2,3-di and 3,4-di compounds are not as stable as the 2,4-di compound (compound 104).

Polymethyl(methacrylate) Films

Polymethyl (methacrylate) films, 1 mil thick, are cast from room temperature methylene chloride solutions of polymethyl (methacrylate), medium molecular weight, Aldrich and between 1 and 3% benzylidene malonate derivative (wt % based on polymer) using a calibrated drawdown bar. The free standing films are mounted in cardboard holders, secured In metal frames and exposed in an Atlas Ci65 xenon arc weatherometer under dry conditions (ASTM G26). Loss of UVA is determined by monitoring loss of diagnostic UV absorbance. To eliminate scatter due to excessive noise in the UV spectra at 0 hours, data on rate loss is tabulated beginning at 1000 hours after a smooth loss rate is observed and measured at 300, 310 and 320 nm rather than only at lambda max.

PR25, 1.4%

| | Absorbance | | | | |
|---|---|---|---|---|---|
| wavelength (nm) | 1000 h | 1500 h | 2000 h | ΔA | ΔA/100 |
| 300 | 2.95 | 2.67 | 2.37 | 0.58 | 0.06 |
| 310 | 3.21 | 3.06 | 2.77 | 0.44 | 0.04 |
| 320 | 3.19 | 2.86 | 2.51 | 0.68 | 0.07 |

Compound 104 1.57%

| | Absorbance | | | | |
|---|---|---|---|---|---|
| wavelength (nm) | 1000 h | 1500 h | 2000 h | ΔA | ΔA/100 |
| 300 | 2.97 | 2.76 | 2.51 | 0.46 | 0.05 |
| 310 | 3.12 | 2.89 | 2.65 | 0.47 | 0.05 |
| 320 | 3.77 | 3.55 | 3.23 | 0.54 | 0.05 |

Compound 141, 1.74%

| | Absorbance | | | | |
|---|---|---|---|---|---|
| wavelength (nm) | 1000 h | 1500 h | 2000 h | ΔA | ΔA/100 |
| 300 | 2.35 | 2.27 | 2.16 | 0.19 | 0.02 |
| 310 | 3.14 | 3.02 | 2.93 | 0.21 | 0.02 |
| 320 | 3.53 | 3.33 | 3.23 | 0.30 | 0.03 |

The compounds of the instant invention, 104 and 141 are as stable or more stable in PMMA than the commercial benzylidene malonate PR25.

The combined data from the above examples demonstrates the desirable spectral and durabilty chartacteristics of the di and tri substituted benzylidene malonates substituted at the 2-position vs. those substituted at the 3-position.

The compounds employed are:

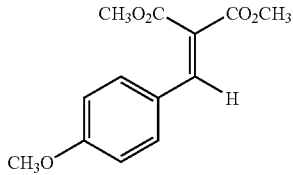

PR25, Sanduvor® PR25, dimethyl p-methoxybenzylidenemalonate (CAS# 7443-25-6)

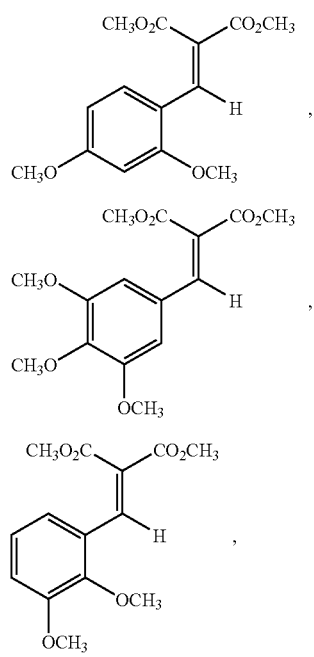

compound 104 compound 3,4,5-tri compound 2,3-di

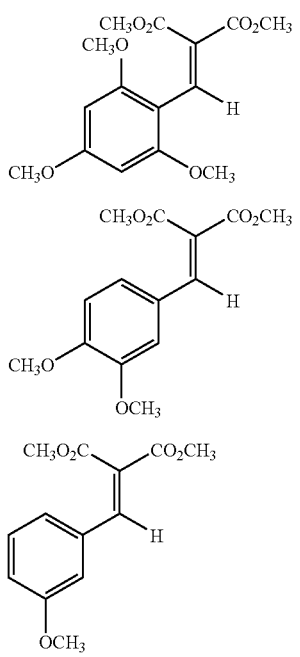

compound 141 compound 3,4-di compound 3-mono

The invention claimed is:
1. A benzoxazinone compound of the formula

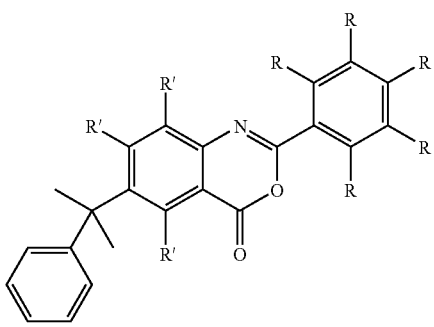

where
each R and R' is independently hydrogen, halogen, straight or branched chain alkoxy of 1 to 24 carbon atoms, cycloalkoxy of 5 to 12 carbon atoms, perfluoroalkoxy of 1 to 24 carbon atoms, cyano, perfluoroalkyl of 1 to 12 carbon atoms, —CO-$G_3$, —COO$G_3$, —CONH$G_3$, —CON($G_3$)$_2$, $E_3$S—, $E_3$SO$_2$—, nitro, —N($G_3$)$_2$, $G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms, or each R and R' is independently hydroxy, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, aryl of 6 to 12 carbon atoms, or said aryl or said phenylalkyl substituted on the aryl ring by 1 to 4 alkyl of 1 to 4 carbon atoms;

or each R and R' is independently said alkyl of 1 to 24 carbon atoms or said alkoxy of 1 to 24 carbon atoms or said alkenyl of 2 to 18 carbon atoms substituted by one or more —OH, —COO$G_3$, —OCO$G_3$, —O$E_4$, —NCO, —NHCO$G_3$ or —N$E_7E_8$ groups or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —N$E_4$- groups or mixtures thereof and which can be unsubstituted or substituted by one or more —OH, —NH$_2$ or —COO$G_3$ or mixtures thereof, or each R and R' is independently a group of formula

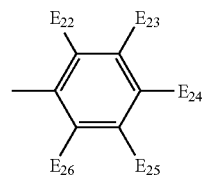

where
$E_{22}$, $E_{23}$, $E_{24}$, $E_{25}$ and $E_{26}$ are independently hydrogen, halogen, straight or branched alkyl of 1 to 18 carbon atoms, alkenyl of 2 to 18 carbon atoms, said alkyl or said alkenyl substituted by one or more halogen, —OCO$G_3$, —O$E_4$, —NCO, —NHCO$G_3$ or —N$E_7E_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$- groups or mixtures thereof and which can be unsubstituted or substituted by one or more —OH, or —NH$_2$, or mixtures thereof; or $E_{22}$, $E_{23}$, $E_{24}$, $E_{25}$ and $E_{26}$ are independently phenyl, phenylalkyl of 7 to 15 carbon atoms, —OH, —OCOG$_3$, —OE$_3$, —NCO, —NHCOG$_3$ or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —SO$_2$—X$_1$-E$_3$;

X$_1$ is —O—, —NH— or —NE$_4$-;

$E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 12 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, $E_7$ and $E_8$ are independently hydrogen, alkyl of 1 to 18 carbon atoms, C$_6$–C$_{14}$aryl, C$_7$–C$_{15}$aralkyl, straight or branched chain alkenyl of 2 to 18 carbon atoms, C$_5$–C$_{12}$cycloalkyl, C$_6$–C$_{14}$aryl or C$_1$–C$_3$hydroxylalkyl, or $E_7$ and $E_8$ together with the N atom are a pyrrolidine, piperidine, piperazine or morpholine ring, where at least one R is halogen, cyano, perfluoroalkyl of 1 to 12 carbon atoms, —CO-G$_3$, —COOG$_3$, —CONHG$_3$, —CON(G$_3$)$_2$, E$_3$SO—, E$_3$SO$_2$—, nitro or a group

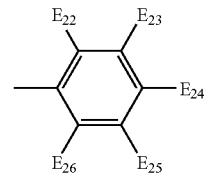

where at least one of $E_{22}$–$E_{26}$ is halogen, cyano, perfluoroalkyl of 1 to 12 carbon atoms, —CO-G$_3$, —COOG$_3$, —CONHG$_3$, —CON(G$_3$)$_2$, E$_3$SO—, E$_3$SO$_2$— or nitro.

2. A compound according to claim 1 where one of R is nitro, E$_3$SO$_2$—, —CO-G$_3$, —COOG$_3$, —CONHG$_3$ or —CON(G$_3$)$_2$.

3. A compound according to claim 1 where at least one of R is —CF$_3$.

* * * * *